US010406221B2

(12) United States Patent
Leng et al.

(10) Patent No.: US 10,406,221 B2
(45) Date of Patent: Sep. 10, 2019

(54) LIPIDATED STREPTOCOCCUS PNEUMONIAE ANTIGEN COMPOSITIONS, METHODS OF PREPARATION AND USE

(71) Applicants: NATIONAL RESEARCH COUNCIL OF CANADA, Ottawa (CA); NATIONAL HEALTH RESEARCH INSTITUTES, Zhunan (CN)

(72) Inventors: Chih-Hsiang Leng, Taipei (CN); Wangxue Chen, Ottawa (CA); Pele Chong, Zhunan (CN)

(73) Assignees: NATIONAL RESEARCH COUNCIL OF CANADA, Ottawa (CA); NATIONAL HEALTH RESEARCH INSTITUTES, Zhunan, Taiwan (CN)

( * ) Notice: Subject to any disclaimer, the term of this patent is extended or adjusted under 35 U.S.C. 154(b) by 0 days.

(21) Appl. No.: 15/619,075

(22) Filed: Jun. 9, 2017

(65) Prior Publication Data

US 2017/0368159 A1  Dec. 28, 2017

Related U.S. Application Data

(63) Continuation-in-part of application No. PCT/CA2016/051449, filed on Dec. 9, 2016.

(60) Provisional application No. 62/265,525, filed on Dec. 10, 2015.

(51) Int. Cl.
| | |
|---|---|
| *C07K 1/00* | (2006.01) |
| *A61K 39/09* | (2006.01) |
| *C07K 16/12* | (2006.01) |
| *C07K 7/08* | (2006.01) |
| *C07K 14/315* | (2006.01) |
| *C12P 21/02* | (2006.01) |
| *C12N 15/63* | (2006.01) |
| *C12N 15/70* | (2006.01) |
| *C07K 19/00* | (2006.01) |
| *A61P 31/04* | (2006.01) |
| *A61K 39/00* | (2006.01) |

(52) U.S. Cl.
CPC ............ *A61K 39/092* (2013.01); *A61P 31/04* (2018.01); *C07K 7/08* (2013.01); *C07K 14/315* (2013.01); *C07K 14/3156* (2013.01); *C07K 16/12* (2013.01); *C07K 19/00* (2013.01); *C12N 15/63* (2013.01); *C12N 15/70* (2013.01); *C12P 21/02* (2013.01); *A61K 2039/6018* (2013.01); *C07K 2319/00* (2013.01); *C07K 2319/21* (2013.01)

(58) Field of Classification Search
CPC .................................................. A61K 39/092
See application file for complete search history.

(56) References Cited

U.S. PATENT DOCUMENTS

| | | | |
|---|---|---|---|
| 4,596,792 | A | 6/1986 | Vyas |
| 4,599,230 | A | 7/1986 | Milich et al. |
| 4,599,231 | A | 7/1986 | Milich et al. |
| 4,601,903 | A | 7/1986 | Frasch |
| 6,217,884 | B1 | 4/2001 | Sampson et al. |
| 6,538,118 | B1 | 3/2003 | Huebner et al. |
| 6,592,876 | B1 | 7/2003 | Briles et al. |
| 7,635,486 | B1 | 12/2009 | Ades et al. |
| 7,883,776 | B2 | 2/2011 | Hukari et al. |
| 7,919,104 | B2 | 4/2011 | Ades et al. |
| 7,960,535 | B2 | 6/2011 | Ades et al. |
| 8,642,048 | B2 | 2/2014 | Ades et al. |
| 8,771,990 | B2 | 7/2014 | Leng et al. |

FOREIGN PATENT DOCUMENTS

| | | |
|---|---|---|
| AU | 734488 | 4/1999 |
| CA | 2756533 A1 | 9/2010 |
| WO | 2009016515 | 2/2009 |
| WO | 2010109324 A1 | 9/2010 |
| WO | 2014018904 A1 | 1/2014 |
| WO | 2016149771 A1 | 9/2016 |

OTHER PUBLICATIONS

Baril et al. "Pneumococcal surface protein A (PspA) is effective at eliciting T cellmediated responses during invasive pneumococcal disease in adults". Clinical and Experimental Immunology, 2006, vol. 145, pp. 277-286.
Briles et al. "Immunization of Humans with Recombinant Pneumococcal Surface Protein a (rPspA) Elicits Antibodies That Passively Protect Mice from Fatal Infection with *Streptococcus pneumoniae* Bearing Heterologous PspA". The Journal of Infectious Diseases, 2000, vol. 182, pp. 1694-1701.
Briles et al. "Immunizations with Pneumococcal Surface Protein A and Pneumolysin Are Protective against Pneumonia in a Murine Model of Pulmonary Infection with *Streptococcus pneumoniae*". The Journal of Infectious Diseases, 2003, vol. 188, pp. 339-348.
Chong et al. "Recombinant Lipoproteins as Novel Vaccines with Intrinsic Adjuvant". Advances in Protein Chemistry and Structural Biology, 2015, vol. 99, pp. 55-74.
Cullen et al. "Construction and evaluation of a plasmid vector for the expression of recombinant lipoproteins in *Escherichia coli*". Plasmid, 2003, vol. 49, pp. 18-29.
De et al. "Purification and characterization of *Streptococcus pneumoniae* palmitoylated pneumococcal surface adhesin A expressed in *Escherichia coli*". Vaccine, 2000, vol. 18, pp. 1811-1821.

(Continued)

*Primary Examiner* — Albert M Navarro
(74) *Attorney, Agent, or Firm* — BCF LLP

(57) ABSTRACT

There are provided compositions and methods for prevention or treatment of *Streptococcus pneumoniae* (SP)-associated diseases. More specifically, there are provided recombinant lipidated fusion proteins comprising pneumococcal surface antigen A (PsaA), the recombinant lipidated fusion proteins comprising, from N-terminus to C-terminus, the N-terminal native lipid signal peptide of PsaA and the C-terminal structural gene for PsaA. Methods of inducing broad spectrum mucosal immunity against SP comprising administering a vaccine comprising recombinant lipidated fusion proteins are also described.

25 Claims, 18 Drawing Sheets

Specification includes a Sequence Listing.

(56) References Cited

OTHER PUBLICATIONS

Fix, Joseph A. "Oral Controlled Release Technology for Peptides: Status and Future Prospects". Pharmaceutical Research, 1996, vol. 13, No. 12, pp. 1760-1764.

Kadioglu et al. "The role of *Streptococcus pneumoniae* virulence factors in host respiratory colonization and disease". Nature Reviews Microbiology, 2008, vol. 6, pp. 288-301.

Kong et al. "Nanogel-Based PspA Intranasal Vaccine Prevents Invasive Disease and Nasal Colonization by *Streptococcus pneumoniae*". Infection and Immunity, 2013, vol. 81, No. 5, pp. 1625-1634.

Kwok et al. "Rapid isolation and characterization of bacterial lipopeptides using liquid chromatography and mass spectrometry analysis". Proteomics, 2011, vol. 11, pp. 2620-2627.

Mitchell et al. "Complement activation and antibody binding by pneumolysin via a region of the toxin homologous to a human acute-phase protein". Molecular Microbiology, 1991, vol. 5, No. 8, pp. 1883-1888.

Miyaji et al. "PsaA (pneumococcal surface adhesin A) and PspA (pneumococcal surface protein A) DNA vaccines induce humoral and cellular immune responses against *Streptococcus pneumoniae*". Vaccine, 2002, vol. 20, pp. 805-812.

O'Brien et al. "Burden of disease caused by *Streptococcus pneumoniae* in children younger than 5 years: global estimates". Lancet, 2009, vol. 374, pp. 893-902.

Ogunniyi et al. "Immunization of Mice with Combinations of Pneumococcal Virulence Proteins Elicits Enhanced Protection against Challenge with Streptococcus pneumoniae". Infection and Immunity, 2000, vol. 68, No. 5, pp. 3028-3033.

Samanen et al. "Chemical Approaches to Improve the Oral Bioavailability of Peptidergic Molecules". J. Pharm. Pharmacol., 1996, vol. 48, pp. 119-135.

Sampson et al. "Cloning and Nucleotide Sequence Analysis of psaA, the *Streptococcus pneumoniae* Gene Encoding a 37-Kilodalton Protein Homologous to Previously Reported *Streptococcus* sp. Adhesins". Infection and Immunity, 1994, vol. 62, No. 1, pp. 319-324.

Tai, Stanley S. "*Streptococcus pneumoniae* Protein Vaccine Candidates: Properties, Activities and Animal Studies", Critical reviews in Microbiology, 2006, vol. 32, No. 3, pp. 139-153.

Talkington et al. "Protection of mice against fatal pneumococcal challenge by immunization with pneumococcal surface adhesin A (PsaA)". Microbial Pathogenesis, 1996, vol. 21, pp. 17-22.

Van Rossum et al. "Host and Bacterial Factors Contributing to the Clearance of Colonization by *Streptococcus pneumoniae* in a Murine Model". Infect. Immun., 2005, vol. 73, No. 11, pp. 7718-7726.

International Search Report and Written Opinion of the International Searching Authority, PCT/CA2016/051449 (WO 2017/096486), dated Mar. 14, 2017.

FIG. 1A

MetLysLysLeuGlyThrLeuLeuValLeuPheLeuSerAlaIle
IleLeuValAlaCysAlaSerGlyLysLysAspThrThrSerGly
GlnLysLeuLysValValAlaThrAsnSerIleIleAlaAspIleThr
LysAsnIleAlaGlyAspLysIleAspLeuHisSerIleValProIle
GlyGlnAspProHisGluTyrGluProLeuProGluAspValLys
LysThrSerGluAlaAspLeuIlePheTyrAsnGlyIleAsnLeuG
luThrGlyGlyAsnAlaTrpPheThrLysLeuValGluAsnAlaLy
sLysThrGluAsnLysAspTyrPheAlaValSerAspGlyValAs
pValIleTyrLeuGluGlyGlnAsnGluLysGlyLysGluAspPro
HisAlaTrpLeuAsnLeuGluAsnGlyIleIlePheAlaLys
AsnIleAlaLysGlnLeuSerAlaLysAspProAsnAsnLysGlu
PheTyrGluLysAsnLeuLysGluTyrThrAspLysLeuAsp
LysLeuAspLysGluSerLysAspLysPheAsnLysIleProAla
GluLysLysLeuIleValThrSerGluGlyAlaPheLysTyrPhe
SerLysAlaTyrGlyValProSerAlaTyrIleTrpGluIleAsnThr
GluGluGluGlyThrProGluGlnIleLysThrLeuValGluLys
LeuArgGlnThrLysValProSerLeuPheValGluSerSerVal
AspAspArgProMetLysThrValSerGlnAspThrAsnIlePro
IleTyrAlaGlnIlePheThrAspSerIleAlaGluGlnGlyLysGlu
GlyAspSerTyrTyrSerMetMetLysTyrAsnLeuAspLysIle
AlaGluGly LeuAlaLysLeuGluHisHisHisHisHisHis***

FIG. 1B

MetAlaSerGlyLysLysAspThrThrSerGlyGlnLysLeuLys
ValValAlaThrAsnSerIleIleAlaAspIleThrLysAsnIleAla
GlyAspLysIleAspLeuHisSerIleValProIleGlyGlnAspPro
HisGluTyrGluProLeuProGluAspValLysLysThrSerGlu
AlaAspLeuIlePheTyrAsnGlyIleAsnLeuGluThrGlyGly
AsnAlaTrpPheThrLysLeuValGluAsnAlaLysLysThrGlu
AsnLysAspTyrPheAlaValSerAspGlyValAspValIleTyr
LeuGluGlyGlnAsnGluLysGlyLysGluAspProHisAlaTrp
LeuAsnLeuGluAsnGlyIleIlePheAlaLysAsnIleAlaLys
GlnLeuSerAlaLysAspProAsnAsnLysGluPheTyrGlu
LysAsnLeuLysGluTyrThrAspLysLeuAspLysLeuAsp
LysGluSerLysAspLysPheAsnLysIleProAlaGluLysLys
LeuIleValThrSerGluGlyAlaPheLysTyrPheSerLysAla
TyrGlyValProSerAlaTyrIleTrpGluIleAsnThrGluGluGlu
GlyThrProGluGlnIleLysThrLeuValGluLysLeuArgGln
ThrLysValProSerLeuPheValGluSerSerValAspAspArg
ProMetLysThrValSerGlnAspThrAsnIleProIleTyrAla
GlnIlePheThrAspSerIleAlaGluGlnGlyLysGluGlyAsp
SerTyrTyrSerMetMetLysTyrAsnLeuAspLysIleAlaGlu
GlyLeuAlaLysLeuGluHisHisHisHisHisHis***

FIG. 1C

MetGluGluSerProValAlaSerGlnSerLysAlaGluLysAsp
TyrAspAlaAlaLysLysAspAlaLysAsnAlaLysLysAlaVal
GluAspAlaGlnLysAlaLeuAspAspAlaLysAlaAlaGlnLys
LysTyrAspGluAspGlnLysLysThrGluGluLysAlaAlaLeu
GluLysAlaAlaSerGluGluMetAspLysAlaValAlaAlaVal
GlnGlnAlaTyrLeuAlaTyrGlnGlnAlaThrAspLysAlaAla
LysAspAlaAlaAspLysMetIleAspGluAlaLysLysArgGlu
GluGluAlaLysThrLysPheAsnThrValArgAlaMetValVal
ProGluProGluGlnLeuAlaGluThrLysLysLysSerGluGlu
AlaLysGlnLysAlaProGluLeuThrLysLysLeuGluGluAlaL
ysAlaLysLeuGluGluAlaGluLysLysAlaThrGluAlaLysGl
nLysValAspAlaGluGluValAlaProGlnAlaLysIleAla
GluLeuGluAsnGlnValHisArgLeuGluGlnGluLeuLysGlu
IleAspGluSerGluSerGluAspTyrAlaLysGluGlyPheArgA
laProLeuGlnSerLysLeuAspAlaLysLysAlaLysLeuSerL
ysLeuGluGluLeuSerAspLysIleAspGluLeuAspAlaGluIl
eAlaLysLeuGluAspGlnLeuLysAlaAlaGluGluAsnAsn
AsnValGluAspTyrPheLysGluGlyLeuGluLysThrIleAlaA
laLysLysAlaGluLeuGluLysThrGluAlaAspLeuLysLysAl
aValAsnGluProGluLysProAlaProAlaProGluThrPro
AlaProGluAlaProAlaGluGlnProLysProAlaProAlaPro
GlnProAlaProAlaProLysProGluLysProAlaGluGlnPro
LysProGluLysThrAspAspGlnGlnAlaGluGluAspTyrAla
ArgArgSerGluGluGluTyrAsnArgLeuThrGlnGlnGlnPro
ProLysAlaGluLysProAlaProAlaProLysLeuGluHisHis
HisHisHisHis***

FIG. 1D

MetValValHisAlaThrGluAsnGluGlySerThrGlnAlaAla
ThrSerSerAsnMetAlaLysThrGluHisArgLysAlaAlaLys
GlnValValAspGluTyrIleGluLysMetLeuArgGluIleGln
LeuAspArgArgLysHisThrGlnAsnValAlaLeuAsnIleLysL
euSerAlaIleLysThrLysTyrLeuArgGluLeuAsnValLeuGl
uGluLysSerLysAspGluLeuProSerGluIleLysAlaLys
LeuAspAlaAlaPheGluLysPheLysLysAspThrLeuLys
ProGlyGluLysValAlaGluAlaLysLysLysValGluGluAla
LysLysLysAlaGluAspGlnLysGluGluAspArgArgAsnTyr
ProThrAsnThrTyrLysThrLeuGluLeuGluIleAlaGluPheA
spValLysValLysGluAlaGluLeuGluLeuValLysGluGluAl
aLysGluSerArgAsnGluGlyThrIleLysGlnAlaLysGlu
LysValGluSerLysLysAlaGluAlaThrArgLeuGluAsnIle
LysThrAspArgLysLysAlaGluGluGluAlaLysArgLysAlaA
spAlaLysLeuLysGluAlaAsnValAlaThrSerAspGlnGlyLy
sProLysGlyArgAlaLysArgGlyValProGlyGluLeuAla
ThrProAspLysLysGluAsnAspAlaLysSerSerAspSer
SerValGlyGluGluThrLeuProSerSerSerLeuLysSerGly
LysLysValAlaGluAlaGluLysLysValGluGluAlaGluLys
LysAlaLysAspGlnLysGluGluAspArgArgAsnTyrProThr
AsnThrTyrLysThrLeuAspLeuGluIleAlaGluSerAspValL
ysValLysGluAlaGluLeuGluLeuValLysGluGluAlaLys
GluProArgAspGluGluLysIleLysGlnAlaLysAlaLysVal
GluSerLysLysAlaGluAlaThrArgLeuGluAsnIleLysThr
AspArgLysLysAlaGluGluGluAlaLysArgLysAlaAlaGlu
GluAspLysValLysGluLysProAlaGluGlnProGlnProAla
ProAlaThrGlnProGluLysProAlaProLysProGluLysProA
laGluGlnProLysAlaGluLysThrAspAspGlnGlnAlaGluGl
uAspTyrAlaArgArgSerGluGluGluTyrAsnArgLeuThrGl
nGlnGlnProProLysGluLysProAlaGlnProSerThrPro
LysLeuGluHisHisHisHisHisHis

Serotype 14 :

Serotype 19F :

*Serotype 35B:*

*Serotype 3:*

N-terminal fragments of rlipo-Ag473

Lipid-CSQEAK:
m/z 1451.9, 1465.9, and 1479.9

N-terminal fragments of rlipo-D1E3

Lipid-CSQEAK:
m/z 1451.9, 1465.9 and 1479.9

Lipid-CSQEAK:
m/z 1451.9, 1466, 1480, 1492 and 1506

SEQUENCE LISTING

```
<160> NUMBER OF SEQ ID NOS: 11

<210> SEQ ID NO 1
<211> LENGTH: 309
<212> TYPE: PRT
<213> ORGANISM: Streptococcus pneumoniae

<400> SEQUENCE: 1

Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
    50                  55                  60

Asp Pro His Glu Tyr Glu Pro Leu Pro Glu Asp Val Lys Lys Thr Ser
65                  70                  75                  80

Glu Ala Asp Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
    130                 135                 140

Glu Asn Gly Ile Ile Phe Ala Lys Asn Ile Ala Lys Gln Leu Ser Ala
145                 150                 155                 160
```

```
Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
            195                 200                 205

Lys Tyr Phe Ser Lys Ala Tyr Gly Val Pro Ser Ala Tyr Ile Trp Glu
            210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
            275                 280                 285

Gly Asp Ser Tyr Tyr Ser Met Met Lys Tyr Asn Leu Asp Lys Ile Ala
            290                 295                 300

Glu Gly Leu Ala Lys
305

<210> SEQ ID NO 2
<211> LENGTH: 290
<212> TYPE: PRT
<213> ORGANISM: Streptococcus pneumoniae

<400> SEQUENCE: 2

Met Ala Ser Gly Lys Lys Asp Thr Thr Ser Gly Gln Lys Leu Lys Val
1               5                   10                  15

Val Ala Thr Asn Ser Ile Ile Ala Asp Ile Thr Lys Asn Ile Ala Gly
                20                  25                  30

Asp Lys Ile Asp Leu His Ser Ile Val Pro Ile Gly Gln Asp Pro His
            35                  40                  45

Glu Tyr Glu Pro Leu Pro Glu Asp Val Lys Lys Thr Ser Glu Ala Asp
50                  55                  60

Leu Ile Phe Tyr Asn Gly Ile Asn Leu Glu Thr Gly Gly Asn Ala Trp
65                  70                  75                  80

Phe Thr Lys Leu Val Glu Asn Ala Lys Lys Thr Glu Asn Lys Asp Tyr
                85                  90                  95

Phe Ala Val Ser Asp Gly Val Asp Val Ile Tyr Leu Glu Gly Gln Asn
            100                 105                 110

Glu Lys Gly Lys Glu Asp Pro His Ala Trp Leu Asn Leu Glu Asn Gly
            115                 120                 125

Ile Ile Phe Ala Lys Asn Ile Ala Lys Gln Leu Ser Ala Lys Asp Pro
130                 135                 140

Asn Asn Lys Glu Phe Tyr Glu Lys Asn Leu Lys Glu Tyr Thr Asp Lys
145                 150                 155                 160

Leu Asp Lys Leu Asp Lys Glu Ser Lys Asp Lys Phe Asn Lys Ile Pro
                165                 170                 175

Ala Glu Lys Lys Leu Ile Val Thr Ser Glu Gly Ala Phe Lys Tyr Phe
            180                 185                 190

Ser Lys Ala Tyr Gly Val Pro Ser Ala Tyr Ile Trp Glu Ile Asn Thr
            195                 200                 205

Glu Glu Glu Gly Thr Pro Glu Gln Ile Lys Thr Leu Val Glu Lys Leu
            210                 215                 220
```

Arg Gln Thr Lys Val Pro Ser Leu Phe Val Glu Ser Val Asp Asp
225                 230                 235                 240

Arg Pro Met Lys Thr Val Ser Gln Asp Thr Asn Ile Pro Ile Tyr Ala
                245                 250                 255

Gln Ile Phe Thr Asp Ser Ile Ala Glu Gln Gly Lys Glu Gly Asp Ser
            260                 265                 270

Tyr Tyr Ser Met Met Lys Tyr Asn Leu Asp Lys Ile Ala Glu Gly Leu
        275                 280                 285

Ala Lys
    290

<210> SEQ ID NO 3
<211> LENGTH: 379
<212> TYPE: PRT
<213> ORGANISM: Streptococcus pneumoniae

<400> SEQUENCE: 3

Met Glu Glu Ser Pro Val Ala Ser Gln Ser Lys Ala Glu Lys Asp Tyr
1               5                   10                  15

Asp Ala Ala Lys Lys Asp Ala Lys Asn Ala Lys Lys Ala Val Glu Asp
                20                  25                  30

Ala Gln Lys Ala Leu Asp Asp Ala Lys Ala Ala Gln Lys Lys Tyr Asp
            35                  40                  45

Glu Asp Gln Lys Lys Thr Glu Glu Lys Ala Ala Leu Glu Lys Ala Ala
        50                  55                  60

Ser Glu Glu Met Asp Lys Ala Val Ala Ala Val Gln Gln Ala Tyr Leu
65                  70                  75                  80

Ala Tyr Gln Gln Ala Thr Asp Lys Ala Ala Lys Asp Ala Ala Asp Lys
                85                  90                  95

Met Ile Asp Glu Ala Lys Lys Arg Glu Glu Ala Lys Thr Lys Phe
            100                 105                 110

Asn Thr Val Arg Ala Met Val Val Pro Glu Pro Glu Gln Leu Ala Glu
            115                 120                 125

Thr Lys Lys Lys Ser Glu Glu Ala Lys Gln Lys Ala Pro Glu Leu Thr
        130                 135                 140

Lys Lys Leu Glu Glu Ala Lys Ala Lys Leu Glu Glu Ala Glu Lys Lys
145                 150                 155                 160

Ala Thr Glu Ala Lys Gln Lys Val Asp Ala Glu Val Ala Pro Gln
                165                 170                 175

Ala Lys Ile Ala Glu Leu Glu Asn Gln Val His Arg Leu Glu Gln Glu
            180                 185                 190

Leu Lys Glu Ile Asp Glu Ser Glu Ser Glu Asp Tyr Ala Lys Glu Gly
        195                 200                 205

Phe Arg Ala Pro Leu Gln Ser Lys Leu Asp Lys Lys Ala Lys Leu
    210                 215                 220

Ser Lys Leu Glu Glu Leu Ser Asp Lys Ile Asp Glu Leu Asp Ala Glu
225                 230                 235                 240

Ile Ala Lys Leu Glu Asp Gln Leu Lys Ala Ala Glu Glu Asn Asn Asn
                245                 250                 255

Val Glu Asp Tyr Phe Lys Glu Gly Leu Glu Lys Thr Ile Ala Ala Lys
            260                 265                 270

Lys Ala Glu Leu Glu Lys Thr Glu Ala Asp Leu Lys Lys Ala Val Asn
        275                 280                 285

Glu Pro Glu Lys Pro Ala Pro Ala Pro Glu Thr Pro Ala Pro Glu Ala

```
                   290                 295                 300

Pro Ala Glu Gln Pro Lys Pro Ala Pro Ala Pro Gln Pro Ala Pro Ala
305                 310                 315                 320

Pro Lys Pro Glu Lys Pro Ala Glu Gln Pro Lys Pro Glu Lys Thr Asp
                325                 330                 335

Asp Gln Gln Ala Glu Glu Asp Tyr Ala Arg Arg Ser Glu Glu Glu Tyr
                340                 345                 350

Asn Arg Leu Thr Gln Gln Gln Pro Pro Lys Ala Glu Lys Pro Ala Pro
                355                 360                 365

Ala Pro Lys Leu Glu His His His His His His
370                 375

<210> SEQ ID NO 4
<211> LENGTH: 490
<212> TYPE: PRT
<213> ORGANISM: Streptococcus pneumoniae

<400> SEQUENCE: 4

Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
                20                  25                  30

Ser Val Val His Ala Thr Glu Asn Glu Gly Ser Thr Gln Ala Ala Thr
            35                  40                  45

Ser Ser Asn Met Ala Lys Thr Glu His Arg Lys Ala Ala Lys Gln Val
50                  55                  60

Val Asp Glu Tyr Ile Glu Lys Met Leu Arg Glu Ile Gln Leu Asp Arg
65                  70                  75                  80

Arg Lys His Thr Gln Asn Val Ala Leu Asn Ile Lys Leu Ser Ala Ile
                85                  90                  95

Lys Thr Lys Tyr Leu Arg Glu Leu Asn Val Leu Glu Glu Lys Ser Lys
            100                 105                 110

Asp Glu Leu Pro Ser Glu Ile Lys Ala Lys Leu Asp Ala Ala Phe Glu
        115                 120                 125

Lys Phe Lys Lys Asp Thr Leu Lys Pro Gly Glu Lys Val Ala Glu Ala
130                 135                 140

Lys Lys Lys Val Glu Glu Ala Lys Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
        195                 200                 205

Ala Lys Glu Lys Val Glu Ser Lys Lys Ala Glu Ala Thr Arg Leu Glu
210                 215                 220

Asn Ile Lys Thr Asp Arg Lys Lys Ala Glu Glu Ala Lys Arg Lys
225                 230                 235                 240

Ala Asp Ala Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
        275                 280                 285
```

-continued

```
Glu Glu Thr Leu Pro Ser Ser Ser Leu Lys Ser Gly Lys Lys Val Ala
    290                 295                 300
Glu Ala Glu Lys Lys Val Glu Glu Ala Glu Lys Lys Ala Lys Asp Gln
305                 310                 315                 320
Lys Glu Glu Asp Arg Arg Asn Tyr Pro Thr Asn Thr Tyr Lys Thr Leu
                325                 330                 335
Asp Leu Glu Ile Ala Glu Ser Asp Val Lys Val Lys Glu Ala Glu Leu
            340                 345                 350
Glu Leu Val Lys Glu Glu Ala Lys Glu Pro Arg Asp Glu Glu Lys Ile
        355                 360                 365
Lys Gln Ala Lys Ala Lys Val Glu Ser Lys Lys Ala Glu Ala Thr Arg
    370                 375                 380
Leu Glu Asn Ile Lys Thr Asp Arg Lys Lys Ala Glu Glu Ala Lys
385                 390                 395                 400
Arg Lys Ala Ala Glu Glu Asp Lys Val Lys Glu Lys Pro Ala Glu Gln
                405                 410                 415
Pro Gln Pro Ala Pro Ala Thr Gln Pro Glu Lys Pro Ala Pro Lys Pro
            420                 425                 430
Glu Lys Pro Ala Glu Gln Pro Lys Ala Glu Lys Thr Asp Asp Gln Gln
        435                 440                 445
Ala Glu Glu Asp Tyr Ala Arg Arg Ser Glu Glu Tyr Asn Arg Leu
    450                 455                 460
Thr Gln Gln Gln Pro Pro Lys Thr Glu Lys Pro Ala Gln Pro Ser Thr
465                 470                 475                 480
Pro Lys Leu Glu His His His His His His
            485                 490
```

<210> SEQ ID NO 5
<211> LENGTH: 20
<212> TYPE: PRT
<213> ORGANISM: Streptococcus pneumoniae

<400> SEQUENCE: 5

```
Met Lys Lys Leu Gly Thr Leu Leu Val Leu Phe Leu Ser Ala Ile Ile
1               5                   10                  15
Leu Val Ala Cys
            20
```

<210> SEQ ID NO 6
<211> LENGTH: 954
<212> TYPE: DNA
<213> ORGANISM: Streptococcus pneumoniae

<400> SEQUENCE: 6

```
atgaaaaaac tgggcaccct gctggtgctg tttctgagcg cgattattct ggtggcgtgc      60
gcgagcggca aaaagatac caccagcggc agaaactga agtggtggc gaccaacagc        120
attattgcgg atattaccaa aaacattgcg ggcgataaaa ttgatctgca tagcattgtg     180
ccgattggcc aggatccgca tgaatatgaa ccgctgccgg aagatgtgaa aaaaaccagc    240
gaagcggatc tgattttttta aacggcatt aacctggaaa ccggcggcaa cgcgtggttt     300
accaaactgg tggaaaacgc gaaaaaaacc gaaaacaaag attattttgc ggtgagcgat    360
ggcgtggatg tgatttatct ggaaggccag aacgaaaaag gcaaagaaga tccgcatgcg   420
tggctgaacc tggaaaacgg cattattttt gcgaaaaaca ttgcgaaaca gctgagcgcg   480
aaagatccga caacaaaga tttttatgaa aaaaacctga agaatatac cgataaactg     540
```

-continued

```
gataaactgg ataaagaaag caaagataaa tttaacaaaa ttccggcgga aaaaaaactg      600
attgtgacca gcgaaggcgc gtttaaatat tttagcaaag cgtatggcgt gccgagcgcg      660
tatatttggg aaattaacac cgaagaagaa ggcacccccgg aacagattaa aaccctggtg     720
gaaaaactgc gtcagaccaa agtgccgagc ctgtttgtgg aaagcagcgt ggatgatcgt      780
ccgatgaaaa ccgtgagcca ggataccaac attccgattt atgcgcagat ttttaccgat      840
agcattgcgg aacagggcaa agaaggcgat agctattata gcatgatgaa atataacctg      900
gataaaattg cggaaggcct ggcgaaactc gagcaccacc accaccacca ctga            954
```

<210> SEQ ID NO 7
<211> LENGTH: 315
<212> TYPE: PRT
<213> ORGANISM: Streptococcus pneumoniae

<400> SEQUENCE: 7

```
Met Lys Lys Leu Gly Thr Leu Leu Val Leu Phe Leu Ser Ala Ile Ile
1               5                   10                  15

Leu Val Ala Cys Ala Ser Gly Lys Lys Asp Thr Ser Gly Gln Lys
            20                  25                  30

Leu Lys Val Val Ala Thr Asn Ser Ile Ile Ala Asp Ile Thr Lys Asn
        35                  40                  45

Ile Ala Gly Asp Lys Ile Asp Leu His Ser Ile Val Pro Ile Gly Gln
    50                  55                  60

Asp Pro His Glu Tyr Glu Pro Leu Pro Glu Asp Val Lys Lys Thr Ser
65                  70                  75                  80

Glu Ala Asp Leu Ile Phe Tyr Asn Gly Ile Asn Leu Glu Thr Gly Gly
                85                  90                  95

Asn Ala Trp Phe Thr Lys Leu Val Glu Asn Ala Lys Lys Thr Glu Asn
            100                 105                 110

Lys Asp Tyr Phe Ala Val Ser Asp Gly Val Asp Val Ile Tyr Leu Glu
        115                 120                 125

Gly Gln Asn Glu Lys Gly Lys Glu Asp Pro His Ala Trp Leu Asn Leu
    130                 135                 140

Glu Asn Gly Ile Ile Phe Ala Lys Asn Ile Ala Lys Gln Leu Ser Ala
145                 150                 155                 160

Lys Asp Pro Asn Asn Lys Glu Phe Tyr Glu Lys Asn Leu Lys Glu Tyr
                165                 170                 175

Thr Asp Lys Leu Asp Lys Leu Asp Lys Glu Ser Lys Asp Lys Phe Asn
            180                 185                 190

Lys Ile Pro Ala Glu Lys Lys Leu Ile Val Thr Ser Glu Gly Ala Phe
        195                 200                 205

Lys Tyr Phe Ser Lys Ala Tyr Gly Val Pro Ser Ala Tyr Ile Trp Glu
    210                 215                 220

Ile Asn Thr Glu Glu Glu Gly Thr Pro Glu Gln Ile Lys Thr Leu Val
225                 230                 235                 240

Glu Lys Leu Arg Gln Thr Lys Val Pro Ser Leu Phe Val Glu Ser Ser
                245                 250                 255

Val Asp Asp Arg Pro Met Lys Thr Val Ser Gln Asp Thr Asn Ile Pro
            260                 265                 270

Ile Tyr Ala Gln Ile Phe Thr Asp Ser Ile Ala Glu Gln Gly Lys Glu
        275                 280                 285

Gly Asp Ser Tyr Tyr Ser Met Met Lys Tyr Asn Leu Asp Lys Ile Ala
    290                 295                 300
```

```
Glu Gly Leu Ala Lys His His His His His
305                 310                 315

<210> SEQ ID NO 8
<211> LENGTH: 296
<212> TYPE: PRT
<213> ORGANISM: Streptococcus pneumoniae

<400> SEQUENCE: 8

Met Ala Ser Gly Lys Lys Asp Thr Thr Ser Gly Gln Lys Leu Lys Val
1               5                   10                  15

Val Ala Thr Asn Ser Ile Ile Ala Asp Ile Thr Lys Asn Ile Ala Gly
            20                  25                  30

Asp Lys Ile Asp Leu His Ser Ile Val Pro Ile Gly Gln Asp Pro His
        35                  40                  45

Glu Tyr Glu Pro Leu Pro Glu Asp Val Lys Lys Thr Ser Glu Ala Asp
    50                  55                  60

Leu Ile Phe Tyr Asn Gly Ile Asn Leu Glu Thr Gly Gly Asn Ala Trp
65                  70                  75                  80

Phe Thr Lys Leu Val Glu Asn Ala Lys Lys Thr Glu Asn Lys Asp Tyr
                85                  90                  95

Phe Ala Val Ser Asp Gly Val Asp Val Ile Tyr Leu Glu Gly Gln Asn
            100                 105                 110

Glu Lys Gly Lys Glu Asp Pro His Ala Trp Leu Asn Leu Glu Asn Gly
        115                 120                 125

Ile Ile Phe Ala Lys Asn Ile Ala Lys Gln Leu Ser Ala Lys Asp Pro
    130                 135                 140

Asn Asn Lys Glu Phe Tyr Glu Lys Asn Leu Lys Glu Tyr Thr Asp Lys
145                 150                 155                 160

Leu Asp Lys Leu Asp Lys Glu Ser Lys Asp Lys Phe Asn Lys Ile Pro
                165                 170                 175

Ala Glu Lys Lys Leu Ile Val Thr Ser Glu Gly Ala Phe Lys Tyr Phe
            180                 185                 190

Ser Lys Ala Tyr Gly Val Pro Ser Ala Tyr Ile Trp Glu Ile Asn Thr
        195                 200                 205

Glu Glu Glu Gly Thr Pro Glu Gln Ile Lys Thr Leu Val Glu Lys Leu
    210                 215                 220

Arg Gln Thr Lys Val Pro Ser Leu Phe Val Glu Ser Ser Val Asp Asp
225                 230                 235                 240

Arg Pro Met Lys Thr Val Ser Gln Asp Thr Asn Ile Pro Ile Tyr Ala
                245                 250                 255

Gln Ile Phe Thr Asp Ser Ile Ala Glu Gln Gly Lys Glu Gly Asp Ser
            260                 265                 270

Tyr Tyr Ser Met Met Lys Tyr Asn Leu Asp Lys Ile Ala Glu Gly Leu
        275                 280                 285

Ala Lys His His His His His His
    290                 295

<210> SEQ ID NO 9
<211> LENGTH: 290
<212> TYPE: PRT
<213> ORGANISM: Streptococcus pneumoniae

<400> SEQUENCE: 9

Cys Ala Ser Gly Lys Lys Asp Thr Thr Ser Gly Gln Lys Leu Lys Val
1               5                   10                  15
```

```
Val Ala Thr Asn Ser Ile Ile Ala Asp Ile Thr Lys Asn Ile Ala Gly
                20                  25                  30

Asp Lys Ile Asp Leu His Ser Ile Val Pro Ile Gly Gln Asp Pro His
         35                  40                  45

Glu Tyr Glu Pro Leu Pro Glu Asp Val Lys Lys Thr Ser Glu Ala Asp
 50                  55                  60

Leu Ile Phe Tyr Asn Gly Ile Asn Leu Glu Thr Gly Gly Asn Ala Trp
 65                  70                  75                  80

Phe Thr Lys Leu Val Glu Asn Ala Lys Lys Thr Glu Asn Lys Asp Tyr
                 85                  90                  95

Phe Ala Val Ser Asp Gly Val Asp Val Ile Tyr Leu Glu Gly Gln Asn
                100                 105                 110

Glu Lys Gly Lys Glu Asp Pro His Ala Trp Leu Asn Leu Gly Asn Gly
            115                 120                 125

Ile Ile Phe Ala Lys Asn Ile Ala Lys Gln Leu Ser Ala Lys Asp Pro
        130                 135                 140

Asn Asn Lys Glu Phe Tyr Glu Lys Asn Leu Lys Glu Tyr Thr Asp Lys
145                 150                 155                 160

Leu Asp Lys Leu Asp Lys Glu Ser Lys Asp Lys Phe Asn Lys Ile Pro
                165                 170                 175

Ala Glu Lys Lys Leu Ile Val Thr Ser Glu Gly Ala Phe Lys Tyr Phe
            180                 185                 190

Ser Lys Ala Tyr Gly Val Pro Ser Ala Tyr Ile Trp Glu Ile Asn Thr
        195                 200                 205

Glu Glu Glu Gly Thr Pro Glu Gln Ile Lys Thr Leu Val Glu Lys Leu
    210                 215                 220

Arg Gln Thr Lys Val Pro Ser Leu Phe Val Glu Ser Ser Val Asp Asp
225                 230                 235                 240

Arg Pro Met Lys Thr Val Ser Gln Asp Thr Asn Ile Pro Ile Tyr Ala
                245                 250                 255

Gln Ile Phe Thr Asp Ser Ile Ala Glu Gln Gly Lys Glu Gly Asp Ser
            260                 265                 270

Tyr Tyr Ser Met Met Lys Tyr Asn Leu Asp Lys Ile Ala Glu Gly Leu
        275                 280                 285

Ala Lys
    290

<210> SEQ ID NO 10
<211> LENGTH: 5
<212> TYPE: PRT
<213> ORGANISM: Streptococcus pneumoniae

<400> SEQUENCE: 10

Cys Ala Ser Gly Lys
1               5

<210> SEQ ID NO 11
<211> LENGTH: 6
<212> TYPE: PRT
<213> ORGANISM: Artificial sequence
<220> FEATURE:
<223> OTHER INFORMATION: synthetic

<400> SEQUENCE: 11

His His His His His His
1               5
```

LIPIDATED *STREPTOCOCCUS PNEUMONIAE* ANTIGEN COMPOSITIONS, METHODS OF PREPARATION AND USE

RELATED APPLICATIONS

The present application is a Continuation-in-Part of PCT/CA2016/051449 filed Dec. 9, 2016, which claims priority to U.S. Provisional Application No. 62/265,525 filed Dec. 10, 2015, the entire contents of each of which are hereby incorporated by reference.

FIELD

The present disclosure provides compositions and methods for prevention or treatment of *Streptococcus pneumoniae* infection. More specifically, the disclosure relates to lipidated *Streptococcus pneumoniae* antigens, methods of preparation thereof, and their use as a vaccine against *Streptococcus pneumoniae*-associated diseases.

BACKGROUND

*Streptococcus pneumoniae* (SP) is the leading bacterial pathogen causing pneumonia, meningitis and sepsis in children. About 1 million children die because of SP infections every year worldwide (O'Brien, K. L., et al., *Lancet* 374: 893-902, 2009).

Current licensed pneumococcal vaccines are exclusively targeted at the capsular polysaccharide (CPS) of SP, and these vaccines provide strictly serotype-specific protection. Although the poor immunogenicity of CPS antigens has been overcome by a pneumococcal CPS-protein conjugate vaccine (PCV), protection is still serotype-specific and the high cost of PCV reduces the vaccination coverage. Moreover, studies of nasopharyngeal colonization by SP have shown that the vacated niche was promptly occupied by non-vaccine pneumococcal serotypes that are potentially capable of causing disease. Thus, in the long term, the widespread introduction of CPS and PCV might merely alter the serotype distribution of invasive pneumococcal disease, without reducing the overall SP disease burden (for review, see Kadioglu, A. et. al., *Nature Reviews Microbiology* 6: 288-301, 2008).

The most promising approach to date has been development of vaccines that are based on pneumococcal antigens that contribute to virulence and are common to all serotypes. Native protein antigens such as PsaA, or immunogenic fragments thereof, can stimulate an immune response when administered to a host, but such antigens are poorly immunogenic and are poor mucosal immunogens. As SP must first gain entry to a host through mucosal surfaces in order to establish an infection, it is desirable to induce mucosal immunity (e.g., mucosal secretory IgA antibodies) in addition to an antigen-specific IgG response. Indeed it has been demonstrated that without induction of Th1 responses, CD4+ T-cell-deficient mice were unable to clear nasopharyngeal colonization.

There is a need for a broad-spectrum pneumococcal vaccine that induces mucosal immunity.

In general, modified proteins, such as lipidated proteins, are more immunogenic than unmodified proteins. Proteins in certain vaccine products have been prepared by expression in *E. coli* using recombinant technology, however, *E. coli* is generally viewed as not suitable for producing modified proteins, particularly lipidated proteins, as *E. coli* cells lipidate naturally lipidated proteins poorly and do not produce non-naturally lipidated proteins in lipidated form.

U.S. Pat. No. 7,833,776 discloses production in *E. coli* of a lipidated fusion protein containing a lipidating sequence derived from Ag473 and a target polypeptide. There is disclosed a lipidating sequence containing at least the N-terminal 40 residues (D1) of Ag473 to facilitate lipidatation in *E. coli* of a fusion protein. Methods of producing a fusion protein in lipidated form are also described.

U.S. Pat. No. 7,960,535 describes recombinant lipidated PsaA proteins and recombinant constructs from which such lipidated PsaA proteins may be expressed. There are described lipidated PsaA proteins in which lipidation is effected by the use of a heterologous leader sequence derived from the ospA gene of *Borrelia burgdorferi*, which leader sequence is joined in translational reading frame with the psaA structural gene. The invention also provides methods of preparation of lipidated PsaA proteins and use of such proteins in immunological compositions. Also provided are vaccines comprising immunogenic lipidated PsaA proteins and methods of use of such vaccines in the prevention and treatment of *S. pneumoniae* infection.

U.S. Pat. No. 6,538,118 describes heterologous lipidated proteins formed recombinantly in an expression system such as *E. coll*. The heterologous lipidated protein has a leader sequence which does not naturally occur with the protein portion of the lipidated protein. The lipidated protein can have the *Borrelia* OspA leader sequence. The protein portion can be OspC, PspA, UreA, Ure B, or a fragment thereof. Methods and compositions for forming and employing the proteins are also disclosed and claimed.

U.S. Pat. No. 8,771,990 describes methods of producing a recombinant lipidated polypeptide in *E. coli*. The method includes providing an *E. coli* host cell adapted to express a recombinant lipidated polypeptide; and culturing the *E. coli* host cell in a minimal medium under conditions that allow expression of the polypeptide in lipidated form.

SUMMARY

It is an object of the present invention to ameliorate at least some of the deficiencies present in the prior art. Embodiments of the present technology have been developed based on the inventors' appreciation that there is a need for improved compositions and methods for prevention and/or treatment of *Streptococcus pneumoniae* (SP) infection and SP-associated diseases.

The present invention is based, at least in part, on the inventors' finding that a recombinant lipidated SP antigen can be produced in *E. coli* using its native lipid signal peptide. Specifically, in contrast to known vaccines that rely on heterologous lipid signal peptides to produce lipidated SP antigens in *E. coli*, the inventors have produced a recombinant lipidated PsaA fusion protein (referred to herein as "rlipo-PsaA") in *E. coli* using the native PsaA lipid signal peptide. Further, rlipo-PsaA induced a mucosal immune response and protected against SP-associated disease in a mouse model. Surprisingly, rlipo-PsaA showed a homogeneous and novel lipid structure, i.e., only a single form of lipid modification is expressed, and the lipid structure is triacyl-lipopeptide (C16:0, C17:1, C16:0), specifically N-acyl-S-diacylglycerol. The immune response elicited in the mouse model was not serotype-specific, e.g., it was protective against more than one serotype of SP. In addition, rlipo-PsaA elicited mucosal immunity against co-administered non-lipidated SP antigens which are otherwise non-immunogenic by themselves, indicating a strong mucosal adjuvant effect for the rlipo-PsaA.

Accordingly, in a first aspect there is provided a recombinant lipidated fusion protein comprising pneumococcal surface antigen A (PsaA), wherein the recombinant lipidated fusion protein comprises, from N-terminus to C-terminus, the N-terminal native lipid signal peptide of PsaA and the C-terminal structural gene for PsaA.

The recombinant lipidated fusion protein may further comprise a tag or a detectable label at the N- or C-terminus. In one embodiment, the recombinant lipidated fusion protein comprises an amino acid tag comprising 6 Histidine residues at the C-terminus.

In some embodiments, the recombinant lipidated fusion protein comprises the native PsaA lipid signal peptide having the amino acid sequence set forth in SEQ ID NO: 5 (MKKLGTLLVLFLSAIILVAC). In some embodiments, the recombinant lipidated fusion protein comprises a lipid signal peptide that is at least about 80-99% identical to the amino acid sequence set forth in SEQ ID NO: 5, e.g., at least about 80%, at least about 85%, at least about 90%, at least about 95%, or at least about 99% identical to the amino acid sequence set forth in SEQ ID NO: 5. In some embodiments, the recombinant lipidated fusion protein comprises a lipid signal peptide comprising the N-terminal portion of PsaA. In some embodiments, the recombinant lipidated fusion protein comprises a lipid signal peptide comprising a maximum length of about 15-40 amino acids.

In some embodiments, the recombinant lipidated fusion protein comprises the amino acid sequence set forth in SEQ ID NO: 1 or 7 (rlipo-PsaA) or a homolog, fragment, analog, or variant thereof. In some embodiments, the recombinant lipidated fusion protein comprises an amino acid sequence at least about 80-99% identical to the amino acid sequence set forth in SEQ ID NO: 1 or 7. The recombinant lipidated fusion protein may comprise an amino acid sequence at least about 80%, at least about 85%, at least about 90%, at least about 95%, or at least about 99% identical to the amino acid sequence set forth in SEQ ID NO: 1 or 7. It should be understood that the recombinant lipidated fusion protein may comprise the full-length PsaA protein or an immunogenic portion thereof. Functionally equivalent or biologically active homologs, fragments, analogs and/or variants thereof are also encompassed.

In some embodiments, the recombinant lipidated fusion protein does not contain the signal peptide (e.g., the amino acid sequence set forth in SEQ ID NO: 5). In such embodiments, the signal peptide is cleaved from the PsaA protein before the lipid modification is added. Typically, the signal peptide is cleaved just before the C-terminal Cysteine of the sequence set forth in SEQ ID NO: 5, to produce the C-terminal structural protein for PsaA having the amino acid sequence set forth in SEQ ID NO: 9. The protein set forth in SEQ ID NO:9 is then lipidated at the N-terminal Cysteine residue to produce rlipo-PSA.

Accordingly, in some embodiments, the recombinant lipidated fusion protein comprises the amino acid sequence set forth in SEQ ID NO: 9 (rlipo-PsaA) or a homolog, fragment, analog, or variant thereof. In some embodiments, the recombinant lipidated fusion protein comprises an amino acid sequence at least about 80-99% identical to the amino acid sequence set forth in SEQ ID NO: 9. The recombinant lipidated fusion protein may comprise an amino acid sequence at least about 80%, at least about 85%, at least about 90%, at least about 95%, or at least about 99% identical to the amino acid sequence set forth in SEQ ID NO: 9. It should be understood that in some embodiments the recombinant lipidated fusion protein may comprise the full-length PsaA protein or an immunogenic portion thereof without the signal peptide, i.e., the full-length PsaA protein generated after cleavage of the signal peptide. Functionally equivalent or biologically active homologs, fragments, analogs and/or variants thereof are also encompassed.

In some embodiments, the recombinant lipidated fusion protein comprises the amino acid sequence set forth in SEQ ID NO: 9 wherein the lipid modification is N-acyl-S-diacylglycerol linked to the N-terminal cysteine. In some embodiments, the recombinant lipidated fusion protein is in isolated or purified form, e.g., isolated from the expression system in which it is produced.

Recombinant lipidated fusion proteins are produced using recombinant techniques and may be produced using any suitable expression system. In some embodiments, recombinant lipidated fusion proteins are expressed in E. coli, e.g., in a strain that provides high-level protein expression such as (without limitation) C43(DE3), (ECCC B96070445), C41(DE3) (ECCC B96070444), C0214(DE3), DK8(DE3)S (NCIMB 40885), or C2014(DE3) (NCIMB 40884), and are optionally isolated or purified therefrom. In one embodiment, recombinant lipidated fusion proteins are produced by expression of a vector comprising the DNA having the nucleotide sequence set forth in SEQ ID NO: 6.

In some embodiments, recombinant lipidated fusion proteins provided herein comprise a homogeneous lipid structure, e.g, a single major peak is observed by mass spectrometry. In an embodiment, a recombinant lipidated fusion protein has the mass spectrometry spectrum shown in FIG. 6D or FIG. 6E. In an embodiment, a recombinant lipidated fusion protein comprises a lipid structure which is triacyl-lipopeptide (C16:0, C17:1, C16:0). In an embodiment, a recombinant lipidated fusion protein comprises a lipid structure which is N-acyl-S-diacylglycerol. In an embodiment, a recombinant lipidated fusion protein comprises an N-terminal fragment which is N-acyl-S-diacylglycerol cysteine-Ala-Ser-Gly-Lys. It should be noted that this N-terminal fragment is distinct from the lipid structure found on other recombinant lipidated fusion proteins, which exhibit unsaturated lipid moieties (e.g., C16 to C19) at the R2 position after the signal sequence is processed and cleaved. In some embodiments, recombinant lipidated fusion proteins provided herein are capable of inducing an immune response, including a mucosal immune response, against SP infection and SP-associated diseases in a subject. The mucosal immune response may comprise a Th1 response and/or production of secretory IgA in the subject. In some embodiments, recombinant lipidated fusion proteins are capable of inducing a mucosal immune response when administered in the absence of an adjuvant.

In some embodiments, recombinant lipidated fusion proteins are further capable of inducing a mucosal immune response against one or more non-lipidated *Streptococcus pneumoniae* (SP) antigen (e.g., pneumococcal surface protein A (PspA), pneumococcal surface protein C (PspC), etc.) administered concomitantly.

The induced immune response may be protective against a wide range of SP-associated diseases, including both acute and chronic disease, such as, without limitation, pneumonia, meningitides, sepsis, ear infection, sinus infection, and bacteremia. In some embodiments, the induced immune response is not serotype-specific.

In another aspect, there are provided methods of producing recombinant lipidated fusion proteins described herein. The methods comprise the steps of: (1) providing a host *E. coli* cell transformed with an expression vector that comprises a first nucleotide sequence encoding the N-terminal native lipid signal peptide of PsaA and a second nucleotide sequence encoding the C-terminal structural gene for PsaA; and (2) cultivating the E. coli transformant to allow expression of the fusion protein comprising the N-terminal native lipid signal peptide of PsaA and the C-terminal structural gene for PsaA. The host E. coli cell may be from a strain that provides high-level protein expression such as, without limitation, C43(DE3), (ECCC B96070445), C41(DE3) (ECCC B96070444), C0214(DE3), DK8(DE3)S (NCIMB 40885), and C2014(DE3) (NCIMB 40884). In some embodiments, the E. coli transformant is cultivated in M9 medium. In some embodiments, the expression vector comprises the nucleotide sequence set forth in SEQ ID NO: 6. In some embodiments, the method further comprises isolating or purifying the recombinant lipidated fusion protein from the E. coli after expression thereof.

In some embodiments, there are provided recombinant lipidated fusion proteins made according to the methods provided herein.

In another aspect, there is provided a composition comprising one or more recombinant lipidated fusion protein described herein and a pharmaceutically acceptable diluent, carrier, or excipient. In some embodiments, the composition further comprises one or more non-lipidated SP antigen such as PspA and/or PspC.

In another aspect, there is provided a vaccine for prevention or treatment of SP-associated diseases comprising one or more recombinant lipidated fusion protein described herein, and an adjuvant. In some embodiments, the vaccine further comprises one or more non-lipidated SP antigen such as PspA and/or PspC.

In yet another aspect, there is provided an isolated antibody or fragment thereof specific for a recombinant lipidated fusion protein described herein. In some embodiments, the antibody or fragment thereof is a polyclonal antibody. In alternative embodiments, the antibody or fragment thereof is a monoclonal antibody. The antibody or fragment thereof may be humanized, human, or chimeric. In some embodiments, the antibody or fragment thereof comprises a whole immunoglobulin molecule; a single-chain antibody; a single-chain variable fragment (scFv); a single domain antibody; an Fab fragment; an F(ab')$_2$ fragment; or a disulfide-linked Fv (di-scFv). The antibody or fragment thereof may comprise a heavy chain immunoglobulin constant domain selected from human IgM, human IgG1, human IgG2, human IgG3, human IgG4, and human IgA½. Further, the antibody or fragment thereof may comprise a light chain immunoglobulin constant domain selected from human Ig kappa and human Ig lambda. In some embodiments, the antibody or fragment binds to an antigen with high affinity constant of $10^7$ M-$10^{10}$ M.

Compositions comprising an isolated antibody or fragment thereof and a pharmaceutically acceptable diluent, carrier, or excipient are also provided.

In some embodiments, compositions provided herein further comprise a second agent for preventing or treating SP infection or SP-associated disease. In some embodiments, the second agent comprises, without limitation, one or more of: an antibody that binds to PspA and an antibody that binds to PspC. In another embodiment, the second agent comprises an antibiotic such as, without limitation, metronidazole or vancomycin.

In another aspect, there are provided methods for preventing or treating SP infection and/or an SP-associated disease comprising administering to a subject the recombinant lipidated fusion proteins, compositions, vaccines, or antibodies or fragments thereof described herein, such that SP infection and/or an SP-associated disease is prevented or treated in the subject. Methods of inducing immunity against SP infection in a subject, such that SP infection is prevented or treated in the subject, are also provided. In some embodiments, methods of inducing mucosal immunity against SP infection in a subject, such that SP infection is prevented or treated in the subject, are provided. Mucosal immunity may, in some embodiments, include one or more of a Th1 response and production of secretory IgA. In some embodiments, methods of inducing non serotype-specific immunity against SP infection in a subject, such that SP infection by more than one serotype is prevented or treated in the subject, are provided.

A recombinant lipidated fusion protein, composition, vaccine, antibody or fragment thereof may be administered intravenously, subcutaneously, intramuscularly, transmucosally, or orally. In some embodiments, a recombinant lipidated fusion protein, composition, vaccine, antibody or fragment thereof is administered in combination with a second agent for preventing or treating SP infection. The second agent may be administered concomitantly with the recombinant lipidated fusion protein, composition, vaccine, antibody or fragment thereof, or they may be administered sequentially, i.e., one before the other.

Use of a recombinant lipidated PsaA fusion protein in the manufacture of a vaccine for prevention or treatment of SP infection is also provided.

In yet another aspect, there are provided kits for preventing or treating SP infection or an SP-associated disease comprising one or more recombinant lipidated fusion protein, antibody, composition, and/or vaccine as described herein. Instructions for use or for carrying out the methods described herein may also be provided in a kit. A kit may further include additional reagents, solvents, buffers, adjuvants, etc., required for carrying out the methods described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to preferred embodiments of the present invention, and in which:

FIGS. 1A-1D show: FIG. 1A: the amino acid sequence of full-length PsaA protein; FIG. 1B: the amino acid sequence of PsaA without signal peptide; FIG. 1C: the amino acid sequence of choline binding domain (CBD)-deleted pneumococcal surface protein A (PspAΔCBD); and FIG. 1D: the amino acid sequence of CBD-deleted PspC (PspCΔCBD).

FIG. 2A: The purification process of rlipo-PsaA was monitored by 15% SDS-PAGE under reducing conditions and with Coomassie Blue staining. Lane 1, cell lysate after IPTG induction; lane 2, cell lysate before IPTG induction; lane 3, soluble fraction of induced cells; lane 4, purified rlipo-PsaA. Lanes 5-8 are the results of immunoblot monitoring of the rlipo-PsaA purification process, using anti-(His)6 antibodies. FIG. 2B: The purification process of rPsaA-Ct was monitored by 15% SDS-PAGE under reducing conditions and with Coomassie Blue staining. Lane 1, cell lysate after IPTG induction; lane 2, cell lysate before IPTG induction; lane 3, soluble fraction of induced cells; lane 4, purified rPsaA-Ct. Lanes 5-8 are the results of immunoblot monitoring of the rPsaA-Ct purification process, using anti-(His)6 antibodies. FIG. 2C: The purification process of rPspAΔCBD was monitored by 15% SDS-PAGE under reducing conditions and with Coomassie Blue staining. Lane 1, cell lysate after IPTG induction; lane 2, cell lysate before IPTG induction; lane 3, soluble fraction of induced cells; lane 4, purified rPspAΔCBD. Lanes 5-8 are the results of immunoblot monitoring of the rPspAΔCBD purification process, using anti-(His)6 antibodies. FIG. 2D: The purification process of rPspCΔCBD was monitored by 15% SDS-PAGE under reducing conditions and with Coomassie Blue staining. Lane 1, cell lysate after IPTG induction; lane 2, cell lysate before IPTG induction; lane 3, soluble fraction of induced cells; lane 4, purified rPspCΔCBD. Lanes 5-8 are the results of immunoblot monitoring of the rPspCΔCBD purification process, using anti-(His)6 antibodies.

FIG. 3A: 10 minutes digested sample was analyzed by Bruker AutoFlex™ III mass spectrometer. The MALDI-TOF MS spectra also demonstrated that the major peak at m/z 1266 was the lipopeptide fragment from the N-terminal of rlipo-PsaA. FIG. 3B: The CD40 molecules were able to be upregulated after stimulation with rlipo-PsaA while the stimulating effects with rPsaA-Ct was not obvious. FIG. 3C: The secretion of TNF-α was induced by rlipo-PsaA in a dose-dependent manner but not by rPsaA-Ct group. FIG. 3D: The IL-12p40 was induced by rlipo-PsaA in a dose-dependent manner but not by rPsaA-Ct group.

FIG. 4A: Mice were immunized twice by subcutaneous injection of 30 μg of rlipo-PsaA in PBS or of 30 μg of rPsaA-Ct in PBS at two-week intervals. The IgG titers elicited by rlipo-PsaA were 1000-fold higher than those elicited by rPsaA-Ct at week 2, 4 and 5. FIG. 4B: The IgA titers elicited upon immunization with rlipo-PsaA were 10000-fold higher than those elicited by rPsaA-Ct at week 2, 4 and 5. FIG. 4C: Subsequently, to analyze the antibody isotypes elicited upon immunization with rlipo-PsaA and rPsaA-Ct at week 5, the induced levels of IgG1 and IgG2b were measured. The IgG1 levels were comparable in both rlipo-PsaA- and rPsaA-Ct-immunized mice. The IgG2b levels in the rlipo-PsaA-immunized mice were higher than those in the rPsaA-Ct-immunized mice. FIG. 4D: The Th1-biased phenomenon can be clearly observed by comparing the IgG2b/IgG1 ratios in these mice.

FIG. 5A shows the first study, in which mice were vaccinated with rlipo-PsaA and rPsaA-Ct, and were then challenged using 10'LD dose of SP. The mice challenged with $2 \times 10^5$ D39 strain (high virulence strain) were 100% protected after being immunized with rlipo-PsaA and about 75% protected after being immunized with rPsaA. FIG. 5B shows a second study, in which the mice were vaccinated with rlipo-PsaA/rPspAΔCBD/rPspCACBD, rPsaA-Ct/rPspAΔCBD/rPspCACBD, rlipo-PsaA, rPsaA-Ct and PBS, and were then challenged using 100×LD dose of SP. The mice challenged with $3.9 \times 10^6$ D39 strain were 83.3%, 50%, 33.3%, 16.7% and 0% protected by the immunization, respectively. FIG. 5C shows additional studies in which the mice were vaccinated with rlipo-PsaA/rPspAΔCBD/rPspCΔCBD (T1+T2+T3), rPsaA-Ct/rPspAΔCBD/rPspCΔCBD (T1+T2+T4), rlipo-PsaA (T3), rPsaA-Ct (T4) with or without adjuvant (CT) and PBS, as indicated, and were then challenged with serotype 14 of S. pneumoniae. FIG. 5D shows additional studies in which the mice were vaccinated with rlipo-PsaA/rPspAΔCBD/rPspCΔCBD (T1+T2+T3), rPsaA-Ct/rPspAΔCBD/rPspCΔCBD (T1+T2+T4), rlipo-PsaA (T3), rPsaA-Ct (T4) with or without adjuvant (CT) and PBS, as indicated, and were then challenged with serotype 19F of S. pneumoniae. FIG. 5E shows additional studies in which the mice were vaccinated with rlipo-PsaA/rPspAΔCBD/rPspCΔCBD (T1+T2+T3), rPsaA-Ct/rPspAΔCBD/rPspCΔCBD (T1+T2+T4), rlipo-PsaA (T3), rPsaA-Ct (T4) with or without adjuvant (CT) and PBS, as indicated, and were then challenged with serotype 35B of S. pneumoniae. FIG. 5F shows additional studies in which the mice were vaccinated with rlipo-PsaA/rPspAΔCBD/rPspCΔCBD (T1+T2+T3), rPsaA-Ct/rPspAΔCBD/rPspCΔCBD (T1+T2+T4), rlipo-PsaA (T3), rPsaA-Ct (T4) with or without adjuvant (CT) and PBS, as indicated, and were then challenged with serotype 3 of S. pneumoniae. The vaccinated mice showed significantly reduced nasopharyngeal colonization by S. pneumoniae serotypes 35B, 14, and 19F or survived the lethal challenges with serotype 3.

FIG. 6A shows that the lipid signal peptide from meningococcal protein Ag473 resulted in at least three peaks, as analyzed by mass spectrometry. FIGS. 6B and 6C show that the antigens D1E3 and E7m respectively fused with the lipid signal peptide of Ag473 also contained at least three peaks. FIGS. 6D and 6E show that, in contrast, rlipo-PsaA expressed using its own native lipid signal peptide expressed as one major peak (molecular weight) (FIGS. 6D and 6E show results from two different batches of rlipo-PsaA).

DETAILED DESCRIPTION

Figure 2A:
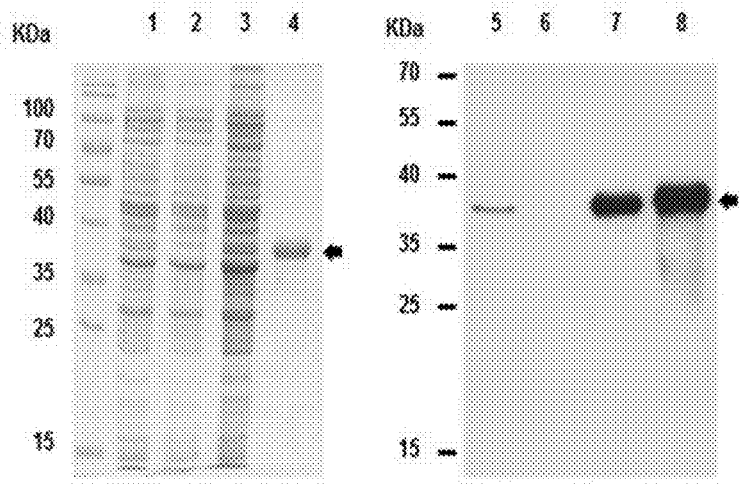
FIGS. 2A-2D show: the purification of selected immunogens, including rlipo-PsaA, rPsaA-Ct, rPspAΔCBD, and rPspCΔCBD.

The present disclosure provides recombinant lipidated fusion proteins comprising PsaA proteins and portions thereof, the fusion proteins comprising the native lipid signal peptide of PsaA, which has not heretofore been possible.

In particular, we report herein that pneumococcal surface antigen A (PsaA), a native lipoprotein, can use its own lipid signal peptide to produce recombinant lipidated protein from an E. coli construct containing a synthetic DNA fragment encoding PsaA. In mouse models, immunization with the recombinant lipidated PsaA fusion protein enhanced PsaA-specific IgG and IgA antibody titers and induced a Th1-biased immune response, as well as protecting the mice against the challenge of different pneumococcal strains. In addition, the recombinant lipidated PsaA fusion protein with other truncated antigens, choline binding domain (CBD)-deleted pneumococcal surface protein A (PspAΔCBD) and CBD-deleted pneumococcal surface protein C (PspCΔCBD), was able to induce an immune response against the co-administered antigens and protect mice against a high-dose challenge, whereas non-lipidated PsaA with PspA and PspC did not provide protection. Recombinant lipidated fusion proteins described herein and compositions thereof are therefore useful as a vaccine against a broad spectrum of SP infection and SP-associated diseases.

In some embodiments, the recombinant lipidated fusion proteins provided herein induce a broad spectrum mucosal immune response against *S. pneumoniae* (SP) in addition to systemic immune responses. Further, the recombinant lipidated fusion proteins can have an adjuvant effect for other co-administered SP antigens, eliciting an immune response against them as well. In some embodiments, the recombinant lipidated fusion proteins may have homogeneous lipid modifications as determined using mass spectrometry. Methods of preparation of the recombinant lipidated fusion proteins and uses thereof as a vaccine against SP-associated diseases are also provided herein.

In some embodiments, recombinant lipidated fusion proteins, compositions and methods of use thereof may provide one or more of the following advantages: ability to induce a protective immune response, including a mucosal immune response, against SP; ability to induce a protective immune response against SP that is not serotype-specific; and/or, ability to induce a mucosal immune response against one or more non-lipidated SP antigen formulated and/or co-administered with the recombinant lipidated PsaA fusion proteins (in other words, having a mucosal adjuvant effect). In some embodiments, provision of a recombinant lipidated PsaA fusion protein comprising the native lipid signal peptide of PsaA provides a lipidated protein with a homogeneous lipid structure, e.g., having only a single form of lipid modification, as determined using mass spectrometry where a single peak is observed. The homogeneous lipid structure may in some cases be advantageous by making manufacturing easier and/or reducing manufacturing costs, by providing a simpler fusion protein product and improved batch-to-batch consistency. In some embodiments, recombinant lipidated fusion proteins provided herein may advantageously increase the specificity and/or reduce the cross-reactivity of the induced immune response, particularly as compared to known antigens that use heterologous lipid modifications (such as meningococcal lipo-antigen, rAg473, fusion antigens, rlipo-D1E3, and rlipo-E7m). Other technical effects may be obtained using recombinant lipidated fusion proteins, compositions and methods of use described herein. It should be understood that not all technical effects and advantages mentioned herein need to be enjoyed in each and every embodiment of the present technology.

Recombinant Lipidated Fusion Proteins

There is provided herein a recombinant lipidated fusion protein comprising pneumococcal surface antigen A (PsaA), wherein the recombinant lipidated fusion protein comprises, from N-terminus to C-terminus, the N-terminal native lipid signal peptide of PsaA and the C-terminal structural gene for PsaA, optionally with a tag or detectable label at the N- or C-terminus.

It should be understood that any immunogenic homolog, analog, variant, or fragment or portion of the recombinant lipidated fusion protein is also encompassed by the present invention, and may be used in compositions and methods provided herein. It is noted that many different strains and serotypes of SP are known and the antigens expressed by different strains and serotypes may vary slightly in their amino acid sequences. However, the recombinant lipidated fusion protein provided herein is not meant to be limited to the PsaA protein expressed by any particular strain or serotype. It is expressly intended that homologs, variants, fragments, and analogs are encompassed by the present technology.

The terms "recombinant lipidated fusion protein" and "recombinant lipidated PsaA fusion protein" are used interchangeably herein to refer to the PsaA fusion proteins comprising the native PsaA lipid signal peptide provided herein, and/or produced according to the recombinant methods provided herein.

The term "lipidated" is used herein to refer to a protein that is covalently modified by binding of a lipid group. Proteins may be covalently modified with a variety of lipids, including fatty acids, isoprenoids, and cholesterol. Lipidation can affect the activity of the protein and/or its subcellular localization and increase immunogenicity of peptide antigens. Lipidated proteins are important for many bacterial infection processes.

The term "recombinant" is used herein to refer to a protein that is produced in vitro or using a recombinant expression system, i.e., expressed from a recombinant construct (such as an expression vector) encoding the protein in a host cell (such as a bacterial or animal cell), and optionally isolated and/or purified from the host cell, or used in an extract from the expression system. Recombinant proteins can typically be produced at high yield and purity and manipulated to maximize desirable activities and minimize undesirable ones.

Generally, recombinant proteins are produced by: constructing a synthetic or semi-synthetic DNA encoding the PsaA fusion protein of interest; integrating the DNA into an expression vector in a manner suitable for expression of the lipidated PsaA fusion protein; transforming an appropriate prokaryotic or eukaryotic host cell with the expression vector; culturing the transformed or transfected host cell so that the lipidated PsaA fusion protein is expressed; and optionally isolating or purifying the recombinantly produced lipidated PsaA fusion protein.

For recombinant expression, the DNA sequence coding for the lipidated PsaA fusion protein may be wholly synthetic, semi-synthetic or the result of modification of the native psaA gene. The expression vector may contain additional sequences for detection or purification of the fusion protein, such as amino acid tags and the like, or for manipulation of the DNA sequences, such as restriction endonuclease cleavage sites, linkers and the like. It will be appreciated by those skilled in the art that different portions of the fusion protein are generally placed contiguous to each other and coupled in a translational open reading frame relationship.

In some embodiments, a DNA fragment encoding a recombinant lipidated PsaA fusion protein described herein is inserted into an expression vector, such as a vector including a strong promoter (e.g., a T7, T5, T3, or SP6 promoter), to construct an expression plasmid. The strong promoter may be inducible, e.g., by isopropyl β-D-thiogalactoside (IPTG). The expression plasmid may then be introduced into an *E. coli* host strain and positive transformants are cultured under suitable conditions for protein expression. In some embodiments, the *E. coli* host strain may be resistant to the toxic effects that can be induced by over-expression of exogenous proteins. Such *E. coli* strains can be identified and generated, for example, by the methods described in U.S. Pat. No. 6,361,966. Examples of such *E. coli* strains include, but are not limited to, C43(DE3) (ECCC B96070445), C41(DE3) (ECCC B96070444), C0214(DE3), DK8(DE3)S (NCIMB 40885), and C2014(DE3) (NCIMB 40884). The recombinant lipidated fusion protein thus expressed may be isolated or purified from the *E. coli* host cells. Lipidation status of the protein may be confirmed using methods known in the art, such as immunoblotting with an anti-lipoprotein antibody or mass spectrometry.

The sequences of the protein/peptide portion of exemplary recombinant lipidated fusion proteins and other SP antigens, and their encoding DNAs, are given in Table 1.

TABLE 1

Amino acid and nucleotide sequences[1] of exemplary recombinant lipidated fusion proteins, their encoding DNAs, and other SP peptide antigens.

| SEQ ID NO. | Amino acid sequence | Name |
|---|---|---|
| 1 | MKKLGTLLVLFLSAIILVACASGKKDTTSGQKLKVVATNSIIADITKNI AGDKIDLHSIVPIGQDPHEYEPLPEDVKKTSEADLIFYNGINLETGGNA WFTKLVENAKKTENKDYFAVSDGVDVIYLEGQNEKGKEDPHAWLNL ENGIIFAKNIAKQLSAKDPNNKEFYEKNLKEYTDKLDKLDKESKDKFN KIPAEKKLIVTSEGAFKYFSKAYGVPSAYIWEINTEEEGTPEQIKTLVEK LRQTKVPSLFVESSVDDRPMKTVSQDTNIPIYAQIFTDSIAEQGKEGDS YYSMMKYNLDKIAEGLAK | Full-length recombinant lipidated PsaA fusion protein (rlipo-PsaA) |
| 2 | MASGKKDTTSGQKLKVVATNSIIADITKNIAGDKIDLHSIVPIGQDPHE YEPLPEDVKKTSEADLIFYNGINLETGGNAWFTKLVENAKKTENKDY FAVSDGVDVIYLEGQNEKGKEDPHAWLNLENGIIFAKNIAKQLSAKDP NNKEFYEKNLKEYTDKLDKLDKESKDKFNKIPAEKKLIVTSEGAFKYF SKAYGVPSAYIWEINTEEEGTPEQIKTLVEKLRQTKVPSLFVESSVDDR PMKTVSQDTNIPIYAQIFTDSIAEQGKEGDSYYSMMKYNLDKIAEGLA K | PsaA without lipid signal peptide (rPsaA-Ct) |
| 3 | MEESPVASQSKAEKDYDAAKKDAKNAKKAVEDAQKALDDAKAAQK KYDEDQKKTEEKAALEKAASEEMDKAVAAVQQAYLAYQQATDKAA KDAADKMIDEAKKREEEAKTKFNTVRAMVVPEPEQLAETKKKSEEA KQKAPELTKKLEEAKAKLEEAEKKATEAKQKVDAEEVAPQAKIAELE NQVHRLEQELKEIDESESEDYAKEGFRAPLQSKLDAKKAKLSKLEELS DKIDELDAEIAKLEDQLKAAEENNNVEDYFKEGLEKTIAAKKAELEKT EADLKKAVNEPEKPAPAPETPAPEAPAEQPKPAPAPQPAPAPKPEKPA EQPKPEKTDDQQAEEDYARRSEEEYNRLTQQQPPKAEKPAPAPKLEH HHHHH | CBD-deleted PspA (PspAΔCBD) |
| 4 | MFASKSERKVHYSIRKFSIGVASVAVASLVMGSVVHATENEGSTQAA TSSNMAKTEHRKAAKQVVDEYIEKMLREIQLDRRKHTQNVALNIKLS AIKTKYLRELNVLEEKSKDELPSEIKAKLDAAFEKFKKDTLKPGEKVA EAKKKVEEAKKKAEDQKEEDRRNYPTNTYKTLELEIAEFDVKVKEAE LELVKEEAKESRNEGTIKQAKEKVESKKAEATRLENIKTDRKKAEEEA KRKADAKLKEANVATSDQGKPKGRAKRGVPGELATPDKKENDAKSS DSSVGEETLPSSSLKSGKKVAEAEKKVEEAEKKAKDQKEEDRRNYPT NTYKTLDLEIAESDVKVKEAELELVKEEAKEPRDEEKIKQAKAKVESK KAEATRLENIKTDRKKAEEEAKRKAAEEDKVKEKPAEQPQPAPATQP EKPAPKPEKPAEQPKPAEKTDDQQAEEDYARRSEEEYNRLTQQQPPKT EKPAQPSTPKLEHHHHHH | CBD-deleted PspC (PspCΔCBD) |
| 5 | MKKLGTLLVLFLSAIILVAC | PsaA native lipid signal peptide |
| 6 | ATGAAAAAACTGGGCACCCTGCTGGTGCTGTTTCTGAGCGCGATTATTCTGG TGGCGTGCGCGAGCGGCAAAAAGATACCACCAGCGGCCAGAAACTGAAAGT GGTGGCGACCAACAGCATTATTGCGGATATTACCAAAAACATTGCGGGCGAT AAAATTGATCTGCATAGCATTGTGCCGATTGGCCAGGATCCGCATGAATATG AACCGCTGCCGGAAGATGTGAAAAAACCAGCGAAGCGGATCTGATTTTTTA TAACGGCATTAACCTGGAAACGGCGGCAACGCGTGGTTTACCAAACTGGTG GAAAACGCGAAAAAACCGAAAACAAAGATTATTTTGCGGTGAGCGATGGCG TGGATGTGATTTATCTGGAAGGCCAGAACGAAAAGGCAAAGAAGATCCGCA TGCGTGGCTGAACCTGGAAAACGGCATTATTTTTGCGAAAAACATTGCGAAA CAGCTGAGCGCGAAAGATCCGAACAACAAAGAATTTTATGAAAAAAACCTGA AAGAATATACCGATAAACTGGATAAACTGGATAAAGAAAGCAAAGATAAATT TAACAAAATTCCGGCGGAAAAAAAACTGATTGTGACCAGCGAAGGCGCGTTT AAATATTTTAGCAAAGCGTATGGCGTGCCGAGCGCGTATATTTGGGAAATTA ACACCGAAGAAGAAGGCACCCCGGAACAGATTAAAACCCTGGTGGAAAAACT GCGTCAGACCAAAGTGCCGAGCCTGTTTGTGGAAAGCAGCGTGGATGATCGT CCGATGAAAACCGTGAGCCAGGATACCAACATTCCGATTTATGCGCAGATTT TTACCGATAGCATTGCGGAACAGGGCAAAGAAGGCGATAGCTATTATAGCAT GATGAAATATAACCTGGATAAAATTGCGGAAGGCCTGGCGAAACTGAGCCAC CACCACCACCACCACTGA | DNA encoding rlipo-PsaA protein |
| 7 | MKKLGTELVEFLSAIILVACASGKKDTTSGQKLKVVATNSIIADITKNI AGDKIDLHSIVPIGQDPHEYEPLPEDVKKTSEADLIFYNGINLETGGNA WFTKLVENAKKTENKDYFAVSDGVDVIYLEGQNEKGKEDPHAWLNL ENGIIFAKNIAKQESAKDPNNKEFYEKNEKEYTDKLDKLDKESKDKFN KIPAEKKLIVTSEGAFKYFSKAYGVPSAYIWEINTEEEGTPEQIKTLVEK LRQTKVPSLFVESSVDDRPMKTVSQDTNIPIYAQIFTDSIAEQGKEGDS YYSMMKYNLDKIAEGLAKHHHHHH | rlipo-PsaA with C-terminal His tag |
| 8 | MASGKKDTTSGQKLKVVATNSIIADITKNIAGDKIDLHSIVPIGQDPHE YEPLPEDVKKTSEADLIFYNGINLETGGNAWFTKLVENAKKTENKDY FAVSDGVDVIYLEGQNEKGKEDPHAWLNLENGIIFAKNIAKQLSAKDP NNKEFYEKNIKEYTDKLDKLDKESKDKFNKIPAEKKLIVTSEGAFKYF | rPsaA-Ct with C-terminal His tag |

TABLE 1-continued

Amino acid and nucleotide sequences[1] of exemplary recombinant lipidated fusion proteins, their encoding DNAs, and other SP peptide antigens.

| SEQ ID NO. | Amino acid sequence | Name |
|---|---|---|
| | SKAYGVPSAYIWEINTEEEGTPEQIKTLVEKLRQTKVPSLFVESSVDDR PMKTVSQDTNIPIYAQIFTDSIAEQGKEGDSYYSMMKYNLDKIAEGLA KHHHHHH | |
| 9 | CASGKKDTTSGQKLKVVATNSIIADITKNIAGDKIDLHSIVPIGQDPHE YEPLPEDVKKTSEADLIFYNGINLETGGNAWFTKLVENAKKTENKDY FAVSDGVDVIYLEGQNEKGKEDPHAWLNLENGIIFAKNIAKQLSAKDP NNKEFYEKNLKEYTDKLDKLDKESKDKFNKIPAEKKLIVTSEGAFKYF SKAYGVPSAYIWEINTEEEGTPEQIKTLVEKLRQTKVPSLFVESSVDDR PMKTVSQDTNIPIYAQIFTDSIAEQGKEGDSYYSMMKYNLDKIAEGLA K | rlipo-PsaA without lipid signal peptide |

[1]Amino acid sequences are shown from N-terminal to C-terminal, and nucleotide sequences are shown from 5' to 3' direction.

Variants, analogs, and fragments of recombinant lipidated PsaA fusion proteins are also encompassed. As used herein, a "variant" refers to an amino acid sequence of the naturally occurring protein or peptide in which a small number of amino acids have been substituted, inserted, or deleted, and which retains the relevant biological activity or function of the starting protein. For example, in the case of an antigen for use in a vaccine, a variant may retain the immunogenic characteristics of the starting protein, sufficient for its intended use in inducing immunity. In the case of an antibody, a variant may retain the antigen-binding properties of the starting protein, sufficient for its intended use in binding specifically to antigen.

In some embodiments, a variant includes one or more conservative amino acid substitutions, one or more non-conservative amino acid substitutions, one or more deletions, and/or one or more insertions. A conservative substitution is one in which an amino acid residue is substituted by another amino acid residue having similar characteristics (e.g., charge or hydrophobicity). In general, a conservative amino acid substitution will not substantially change the functional properties of a protein. Examples of groups of amino acids that have side chains with similar chemical properties include: 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Exemplary conservative amino acids substitution groups are: valine-leucine-isoleucine, phenylalanine-tyrosine, lysine-arginine, alanine-valine, glutamate-aspartate, and asparagine-glutamine. Other conservative amino acid substitutions are known in the art and are included herein. Non-conservative substitutions, such as replacing a basic amino acid with a hydrophobic one, are also well-known in the art.

As used herein, an "analog" refers to an amino acid sequence of the naturally occurring protein in which one or more amino acids have been replaced by amino acid analogs. Non-limiting examples of amino acid analogs include non-naturally occurring amino acids, synthetic amino acids, amino acids which only occur naturally in an unrelated biological system, modified amino acids from mammalian systems, polypeptides with substituted linkages, as well as other modifications known in the art, both naturally occurring and non-naturally occurring. In some embodiments, analogs include modifications which increase glycoprotein or glycopeptide stability. In one embodiment, an analog includes a beta amino acid, a gamma amino acid, or a D-amino acid.

A "fragment" refers to a portion of the starting molecule which retains the relevant biological activity or function (e.g, antigenicity, antigen-binding, immunogenicity) of the starting molecule.

A "biologically active" or "functionally equivalent" fragment, variant, or analog generally retains biological activity or function of the starting molecule, sufficient for use in the present compositions and methods. Thus, a "biologically active" or "functionally equivalent" fragment, variant, or analog may retain the binding specificity, the antigenicity, or the immunogenicity of the starting molecule. In some embodiments, a fragment, variant or analog has at least about 70%, at least about 80%, at least about 85%, at least about 90%, at least about 95%, at least about 98%, or at least about 99% sequence identity to the starting molecule (e.g., protein). When referring to an antibody, "functionally equivalent" generally refers to a fragment, derivative, variant, analog, or fusion protein of the antibody that maintains sufficient antigen-binding affinity, specificity and/or selectivity for use in the present compositions and methods. The antigen-binding properties of a functionally equivalent antibody or fragment need not be identical to those of the reference antibody so long as they are sufficient for use in the present compositions and methods for preventing or treating *Streptococcus pneumoniae*-associated diseases.

Variants, fragments, or analogs may also be modified at the N- and/or C-terminal ends to allow the polypeptide or fragment to be conformationally constrained and/or to allow coupling to an immunogenic carrier.

There are further provided conjugated lipidated PsaA antigens comprising a recombinant lipidated PsaA fusion protein conjugated to a carrier molecule. A carrier molecule may be any suitable molecule such as, without limitation, a peptide, a protein, a membrane protein, a carbohydrate moiety, or one or more liposomes loaded with any of the previously recited types of carrier molecules or loaded with a lipidated PsaA antigen itself. Many such carrier molecules are known in the art and may be used in the conjugated lipidated PsaA antigens provided herein. Further, a carrier molecule may be linked to a lipidated PsaA antigen using any suitable method known in the art, for example by a covalent bond or an ionic interaction, either directly or using a linker.

In another embodiment, a lipidated PsaA antigen is produced as a fusion protein or a conjugate that contains other distinct amino acid sequences that are not part of the native SP PsaA sequence, such as amino acid linkers or immunogenic carriers, as well as ligands useful in protein purification, such as glutathione-S-transferase, a histidine tag, and staphylococcal protein A. A heterologous polypeptide can be fused, for example, to the N-terminus or C-terminus of a recombinant lipidated PsaA fusion protein.

As used herein, the term "isolated" refers to a molecule that by virtue of its origin or source of derivation (1) is not associated with naturally associated components that accompany it in its native state, (2) is free of other macromolecules (e.g., proteins, glycans) from the same species, (3) is expressed by a cell from a different species, or (4) does not occur in nature. Thus, a lipidated protein that is chemically synthesized or synthesized in a cellular system different from the cell from which it naturally originates will be "isolated" from its naturally associated components. A lipidated protein may also be rendered substantially free of naturally associated components by isolation, using purification or separation techniques well-known in the art. Recombinant lipidated PsaA fusion proteins used in compositions and methods described herein are generally provided in purified or substantially purified form, i.e., substantially free from other proteins and polypeptides, particularly from other SP or host cell proteins or polypeptides. In some embodiments, recombinant lipidated PsaA fusion proteins are at least about 50% pure, at least about 60% pure, at least about 70% pure, at least about 80%, at least about 90% pure, or at least about 95% pure (by weight).

Recombinant lipidated PsaA fusion proteins can be prepared by various means (e.g., recombinant expression, purification from cell culture, chemical synthesis, etc.). In some embodiments, a recombinant lipidated PsaA fusion protein is purified after expression in a heterologous cell. For example, as outlined above, a polynucleotide encoding a recombinant lipidated PsaA fusion protein can be introduced into an expression vector that can be expressed in a suitable expression system using techniques well-known in the art, followed by isolation or purification of the expressed fusion protein. Typically, a recombinant lipidated PsaA fusion protein is expressed in a heterologous bacterial cell such as *E. coli*. A variety of bacterial expression systems are available in the art and any such suitable expression system can be used.

Many variations of techniques described herein are known in the art and may be used to prepare recombinant lipidated PsaA fusion proteins.

Pharmaceutical Compositions and Methods

There are provided herein compositions and methods for the prevention or treatment of SP infection and/or SP-associated diseases in a subject comprising recombinant lipidated PsaA fusion proteins. Compositions and methods for inducing an immune response to SP are also provided. Methods provided herein comprise administration of a recombinant lipidated PsaA fusion protein to a subject in an amount effective to induce an immune response against SP, thereby reducing, eliminating, preventing, or treating SP-associated diseases. Compositions and methods are also provided for the generation of antibodies for use in passive immunization against SP-associated diseases.

*Streptococcus pneumoniae* (SP) is a pathogenic bacterium that causes many types of pneumococcal infections. There are over ninety known capsular serotypes of SP, of which twenty-three account for about 85-90% of pneumococcal disease. In addition to the most common infections, pneumonia and meningitis, SP also causes pneumococcal diseases such as, without limitation, sepsis, bronchitis, rhinitis, acute sinusitis, otitis media, conjunctivitis, bacteremia, sepsis, osteomyelitis, septic arthritis, endocarditis, peritonitis, pericarditis, cellulitis, and brain abscess. An SP-associated disease can be the result of an acute infection or a chronic infection. In some embodiments, an SP-associated disease is selected from pneumonia, meningitides, ear infection, sinus infection, and bacteremia.

The terms "subject" and "patient" are used interchangeably herein to refer to a subject in need of prevention or treatment for SP-associated diseases or for an infection associated with SP. A subject may be a vertebrate, such as a mammal, e.g., a human, a non-human primate, a rabbit, a rat, a mouse, a cow, a horse, a goat, or another animal. Animals include all vertebrates, e.g., mammals and non-mammals, such as mice, sheep, dogs, cows, avian species, ducks, geese, pigs, chickens, amphibians, and reptiles. In an embodiment, a subject is a human.

"Treating" or "treatment" refers to either (i) the prevention of infection or reinfection, e.g., prophylaxis, or (ii) the reduction or elimination of symptoms of the disease of interest, e.g., therapy. "Treating" or "treatment" can refer to the administration of a composition comprising a recombinant lipidated PsaA fusion protein described herein, or to the administration of antibodies raised against these fusion proteins. Treating a subject with the composition can prevent or reduce the risk of infection and/or induce an immune response to SP.

Treatment can be prophylactic (e.g., to prevent or delay the onset of the disease, to prevent the manifestation of clinical or subclinical symptoms thereof, or to prevent recurrence of the disease) or therapeutic (e.g., suppression or alleviation of symptoms after the manifestation of the disease). "Preventing" or "prevention" refers to prophylactic administration or vaccination with recombinant lipidated PsaA fusion proteins or compositions thereof in a subject who has not been infected or who is symptom-free and/or at risk of infection.

As used herein, the term "immune response" refers to the response of immune system cells to external or internal stimuli (e.g., antigens, cell surface receptors, cytokines, chemokines, and other cells) producing biochemical changes in the immune cells that result in immune cell migration, killing of target cells, phagocytosis, production of antibodies, production of soluble effectors of the immune response, and the like. An "immunogenic" molecule is one that is capable of producing an immune response in a subject after administration. The terms "mucosal immunity" and "mucosal immune response" are used interchangeably to refer to an immune response at mucosal surfaces, typically involving induction of the common mucosal immune system. A mucosal immune response typically includes production of secretory IgA and/or activation of a Th1 response.

"Active immunization" refers to the process of administering an antigen (e.g., an immunogenic molecule, e.g., a recombinant lipidated PsaA fusion protein described herein) to a subject in order to induce an immune response. In contrast, "passive immunization" refers to the administration of active humoral immunity, usually in the form of pre-made antibodies, to a subject. Passive immunization is a form of short-term immunization that can be achieved by the administration of an antibody or an antigen-binding fragment thereof. Antibodies can be administered in several possible forms, for example as human or animal blood plasma or serum, as pooled animal or human immunoglobulin, as high-titer animal or human antibodies from immunized subjects or from donors recovering from a disease, as polyclonal antibodies, or as monoclonal antibodies. Typically, immunity derived from passive immunization provides immediate protection or treatment but may last for only a short period of time.

In some embodiments, there are provided compositions and methods for active immunization against SP infection and/or SP-associated diseases. Compositions and methods are provided for inducing an immune response to SP bacteria in a subject, comprising administering to the subject a recombinant lipidated PsaA fusion protein, optionally in the presence of an adjuvant, in an amount effective to induce an immune response in the subject. In one embodiment, there is provided a composition comprising an effective immunizing amount of a recombinant lipidated fusion protein provided herein and an adjuvant, wherein the composition is effective to prevent or treat an SP-associated disease in a subject in need thereof. In an embodiment, an adjuvant is not required, i.e., compositions and methods are provided for inducing an immune response to SP bacteria in a subject, comprising administering to the subject a recombinant lipidated fusion protein provided herein and a pharmaceutically acceptable carrier, excipient, or diluent, in an amount effective to induce an immune response in the subject.

In some embodiments, compositions and methods are provided for inducing a mucosal immune response to SP in a subject, e.g., an immune response comprising a Th1 response and/or production of secreted IgA is induced. In some embodiments, a systemic immune response is induced, e.g., antibody isotypes such as IgG are produced. In some embodiments, both mucosal and systemic immune responses are induced.

In some embodiments, the induced immune response is not serotype-specific. As used herein, "not serotype-specific" refers to an immune response that is protective against more than one SP serotype. In other words, in a subject immunized with a particular recombinant lipidated PsaA fusion protein, the induced immune response is protective not only against the serotype from which the fusion protein was derived, but also against one or more additional SP serotype. In some embodiments, compositions and methods described herein can thus provide broad spectrum immunity, including mucosal immunity, against SP.

In some embodiments, compositions and methods further comprise administering the recombinant lipidated PsaA fusion protein in combination with one or more additional SP antigen. An additional SP antigen may include, for example, a capsular polysaccharide antigen, a membrane bound virulence factor, or a surface antigen that can be protective against SP infection. In some embodiments, the additional SP antigen is PspA or PspC. Non-limiting examples of additional SP antigens include pneumococcal beta-galactosidase (BgaA), pneumococcal phosphorylcholine (Chop), pneumococcal enolase (Eno), pneumococcal hyaluronate lyase (Hyl), pneumococcal autolysin A (LytA), pneumococcal neuraminidase (Nan), pneumococcal adhesion and virulence A (PavA), pneumococcal iron acquisition (PiaA), and pneumococcal surface associated Pht Proteins (PhtA, PhtB, PhtD, and PhtE).

In some embodiments, administration of the recombinant lipidated PsaA fusion protein in combination with one or more additional SP antigen induces a mucosal immune response against the one or more additional antigen (in addition to a mucosal immune response against PsaA), even though the one or more additional antigen is not lipidated and/or not immunogenic by itself (i.e., when administered in the absence of the recombinant lipidated PsaA fusion protein). In this way, the recombinant lipidated PsaA fusion protein may have a mucosal adjuvant affect, inducing specific mucosal immunity against non-lipidated antigens with which it is co-formulated and/or co-administered.

Non-limiting examples of such non-lipidated antigens include PspA, PspC, pneumococcal beta-galactosidase (BgaA), pneumococcal phosphorylcholine (Chop), pneumococcal enolase (Eno), pneumococcal hyaluronate lyase (Hyl), pneumococcal autolysin A (LytA), pneumococcal neuraminidase (Nan), pneumococcal adhesion and virulence A (PavA), pneumococcal iron acquisition (PiaA), and pneumococcal surface association of Pht Proteins (PhtA, PhtB, PhtD, and PhtE).

Adjuvants generally increase the specificity and/or the level of immune response. An adjuvant may thus reduce the quantity of antigen necessary to induce an immune response, and/or the frequency of injection necessary in order to generate a sufficient immune response to benefit the subject. Any compound or compounds that act to increase an immune response to an antigen and are suitable for use in a subject (e.g., pharmaceutically-acceptable) may be used as an adjuvant in compositions, vaccines, and methods of the invention. In some embodiments, the adjuvant may be the carrier molecule (for example, but not limited to, cholera toxin B subunit, liposome, etc.) in a conjugated or recombinant antigen. In alternative embodiments, the adjuvant may be an unrelated molecule known to increase the response of the immune system (for example, but not limited to attenuated bacterial or viral vectors, AMVAD, etc.). In one embodiment, the adjuvant may be one that generates a strong mucosal immune response such as an attenuated virus or bacteria, or aluminum salts.

Examples of an adjuvant include, but are not limited to, cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery (See, e.g., Audran R. et al. *Vaccine* 21:1250-5, 2003; and Denis-Mize et al., Cell Immunol., 225:12-20, 2003). Other suitable adjuvants are well-known to those of skill in the art. Alternatively, in some embodiments, recombinant lipidated fusion proteins described herein can be used in vaccines against SP-associated disease without additional adjuvant.

Compositions, formulations and vaccines including one or more PsaA antigen described herein can be prepared by uniformly and intimately bringing into association the antigen and the adjuvant using techniques well-known to those skilled in the art including, but not limited to, mixing, sonication and microfluidation. An adjuvant will typically comprise about 5 to about 10% (v/v) or about 10 to about 50% (v/v) of the composition.

In other embodiments, there are provided compositions and methods for passive immunization comprising an antibody or an antigen-binding fragment thereof specific for PS. As used herein, the term "antibody" refers to any immunoglobulin or intact molecule as well as to fragments thereof that bind to a specific antigen or epitope. Such antibodies include, but are not limited to polyclonal, monoclonal, chimeric, humanized, single chain, Fab, Fab', F(ab')$_2$, F(ab)' fragments, and/or F(v) portions of the whole antibody and variants thereof. All isotypes are emcompassed by this term, including IgA, IgD, IgE, IgG, and IgM.

As used herein, the term "antibody fragment" refers to a functionally equivalent fragment or portion of antibody, i.e., to an incomplete or isolated portion of the full sequence of an antibody which retains the antigen binding capacity (e.g., specificity, affinity, and/or selectivity) of the parent antibody. Non-limiting examples of antigen-binding portions include: (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment, which consists of a VH domain; (vi) an isolated complementarity determining region (CDR); and (vii) a single chain Fv (scFv), which consists of the two domains of the Fv fragment, $V_L$ and $V_H$. Other non-limiting examples of antibody fragments are Fab' fragments; diabodies; linear antibodies; single-chain antibody molecules; and multispecific antibodies formed from antibody fragments.

An intact "antibody" comprises at least two heavy (H) chains and two light (L) chains inter-connected by disulfide bonds. Each heavy chain is comprised of a heavy chain variable region ($V_H$) and a heavy chain constant region. The heavy chain constant region is comprised of three domains, $CH_1$, $CH_2$ and $CH_3$. Each light chain is comprised of a light chain variable region ($V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

As used herein, the term "monoclonal antibody" or "mAb" refers to a preparation of antibody molecules of single molecular composition. A monoclonal antibody composition displays a single binding specificity and affinity for a particular epitope. A "human monoclonal antibody" refers to antibodies displaying a single binding specificity which have variable and constant regions (if present) derived from human germline immunoglobulin sequences. In one aspect, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell. A "humanized antibody" refers to at least one antibody molecule in which the amino acid sequence in the non-antigen binding regions and/or the antigen-binding regions has been altered so that the antibody more closely resembles a human antibody, and still retains its original binding properties. Humanized antibodies are typically antibody molecules from non-human species having one or more CDRs from the non-human species and a framework region from a human immunoglobulin molecule. The term "chimeric antibody" refers to an antibody in which different portions are derived from different animal species, e.g., an antibody having a variable region derived from a murine mAb and a human immunoglobulin constant region.

As used herein, the term "antigen" refers to a substance that prompts the generation of antibodies and can cause an immune response. The terms "antigen" and "immunogen" are used interchangeably herein, although, in the strict sense, immunogens are substances that elicit a response from the immune system, whereas antigens are defined as substances that bind to specific antibodies. An antigen or fragment thereof can be a molecule (i.e., an epitope) that makes contact with a particular antibody. When a recombinant lipidated fusion protein or a fragment thereof is used to immunize a host animal, numerous regions of the lipidated fusion protein can induce the production of antibodies (i.e., elicit the immune response), which bind specifically to the antigen (e.g., given regions or three-dimensional structures on the lipidated fusion protein).

The terms "specific for" or "specifically binding" are used interchangeably to refer to the interaction between an antibody and its corresponding antigen. The interaction is dependent upon the presence of a particular structure of the protein recognized by the binding molecule (i.e., the antigen or epitope). In order for binding to be specific, it should involve antibody binding of the epitope(s) of interest and not background antigens, i.e., no more than a small amount of cross reactivity with other antigens (such as other proteins or lipid structures, host cell proteins, etc.). Antibodies, or antigen-binding fragments, variants or derivatives thereof of the present disclosure can also be described or specified in terms of their binding affinity to an antigen. The affinity of an antibody for an antigen can be determined experimentally using methods known in the art. The term "high affinity" for an antibody typically refers to an equilibrium association constant ($K_{aff}$) of at least about $1\times10^7$ liters/mole, or at least about $1\times10^8$ liters/mole, or at least about $1\times10^9$ liters/mole, or at least about $1\times10^{19}$ liters/mole, or at least about $1\times10^{11}$ liters/mole, or at least about $1\times10^{12}$ liters/mole, or at least about $1\times10^{13}$ liters/mole, or at least about $1\times10^{14}$ liters/mole or greater. $K_D$, the equilibrium dissociation constant, can also be used to describe antibody affinity and is the inverse of $K_{aff}$.

Recombinant lipidated fusion proteins described herein are typically combined with a pharmaceutically acceptable carrier or excipient to form a pharmaceutical composition. Pharmaceutically acceptable carriers can include a physiologically acceptable compound that acts to, e.g., stabilize, or increase or decrease the absorption or clearance rate of a pharmaceutical composition. Generally, a pharmaceutically acceptable carrier must be compatible with the active ingredient of the composition, optionally capable of stabilizing the active ingredient, and not deleterious to the subject to be treated. Physiologically acceptable compounds can include, e.g., phosphate buffered saline, a bicarbonate solution, carbohydrates, such as glucose, sucrose, or dextrans, antioxidants, such as ascorbic acid or glutathione, chelating agents, low molecular weight proteins, compositions that reduce the clearance or hydrolysis of glycopeptides, or excipients or other stabilizers and/or buffers. Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. Detergents can also be used to stabilize or to increase or decrease the absorption of the pharmaceutical composition, including liposomal carriers. Pharmaceutically acceptable carriers and formulations are known to the skilled artisan and are described in detail in the scientific and patent literature, see e.g., the latest edition of Remington's Pharmaceutical Science, Mack Publishing Company, Easton, Pa. ("Remington's"). One skilled in the art would appreciate that the choice of a pharmaceutically acceptable carrier including a physiologically acceptable compound depends, for example, on the mode and route of administration of the lipidated fusion protein, composition, antigen, or antibody of the invention, and on its particular physio-chemical characteristics.

Compositions and vaccines of the present invention may be administered by any suitable means, for example, orally, such as in the form of pills, tablets, capsules, granules or powders; sublingually; buccally; parenterally, such as by subcutaneous, intravenous, intramuscular, intraperitoneal or intrastemal injection or using infusion techniques (e.g., as sterile injectable aqueous or non-aqueous solutions or suspensions); nasally, such as by inhalation spray, aerosol, mist, or nebulizer; topically, such as in the form of a cream, ointment, salve, powder, or gel; transdermally, such as in the form of a patch; transmucosally; or rectally, such as in the form of suppositories. The present compositions may also be administered in a form suitable for immediate release or extended release. Immediate release or extended release may be achieved by the use of suitable pharmaceutical compositions, or, particularly in the case of extended release, by the use of devices such as subcutaneous implants or osmotic pumps.

In some embodiments, pharmaceutical compositions described herein may be administered parenterally, e.g., by subcutaneous injection or intramuscular injection, or using other modes of administration such as suppositories and oral formulations. For suppositories, binders and carriers may include, for example, polyalkalene glycols or triglycerides. Oral formulations may include normally employed incipients such as pharmaceutical grades of saccharine, cellulose, magnesium carbonate and the like. These compositions may take the form of solutions, suspensions, tablets, pills, capsules, sustained release formulations, or powders. Compositions may be prepared as final products for injections, as liquid solutions, or emulsions, for example (See, e.g., U.S. Pat. Nos. 4,601,903; 4,599,231; 4,599,230; and 4,596,792).

It is often advantageous to formulate oral or parenteral compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic or immunogenic effect in association with the required pharmaceutical carrier. Compositions of lipidated fusion proteins, antigens, or antibodies, when administered orally, can be protected from digestion, using methods known in the art (see, e.g., Fix, Pharm Res. 13: 1760-1764, 1996; Samanen, J. Pharm. Pharmacol. 48: 119-135, 1996).

In an embodiment, a composition or vaccine is prepared as an injectable, either as a liquid solution or suspension, or as a solid form which is suitable for solution or suspension in a liquid vehicle prior to injection. In another embodiment, a composition or vaccine is prepared in solid form, emulsified or encapsulated in a liposome vehicle or other particulate carrier used for sustained delivery. For example, a vaccine can be in the form of an oil emulsion, a water-in-oil emulsion, a water-in-oil-in-water emulsion, a site-specific emulsion, a long-residence emulsion, a sticky emulsion, a microemulsion, a nanoemulsion, a liposome, a microparticle, a microsphere, a nanosphere, or a nanoparticle. A vaccine may include a swellable polymer such as a hydrogel, a resorbable polymer such as collagen, or certain polyacids or polyesters such as those used to make resorbable sutures, that allow for sustained release of a vaccine.

In some embodiments, compositions provided herein include one or more additional therapeutic or prophylactic agents for SP-associated diseases. For example, a composition may contain a second agent for preventing or treating SP infection. Examples of such second agents include, without limitation, antibiotics (such as metronidazole and vancomycin) and antibodies (such as antibodies that bind to additional SP antigens such as, without limitation, PspA and PspC).

In alternative embodiments, compositions of the present invention may be employed alone, or in combination with other suitable agents useful in the prevention or treatment of SP-associated disease. In some embodiments, compositions of the present invention are administered concomitantly with a second composition comprising a second therapeutic or prophylactic agent for SP-associated disease.

As used herein, a "therapeutically effective amount" or "an effective amount" refers to an amount of a recombinant lipidated fusion protein, composition, vaccine, antigen, or antibody that is sufficient to prevent or treat an SP-associated disease, to alleviate (e.g., mitigate, decrease, reduce) at least one of the symptoms associated with an SP-associated disease, and/or to induce an immune response to SP, such that benefit to the subject is provided. The effective amount of a composition, vaccine, antigen, or antibody may be determined by one of ordinary skill in the art. Exemplary antigen dosage amounts for an adult human include, without limitation, from about 0.1 to 500 mg/kg of body weight of antigen or antibody per day, which may be administered in a single dose or in the form of individual divided doses, such as from 1 to 5 times per day, or weekly, or bi-weekly.

In some embodiments, an effective amount of a composition comprising a recombinant lipidated fusion protein contains about 0.05 to about 1500 μg protein, about 10 to about 1000 μg protein, about 30 to about 500 μg, or about 40 to about 300 μg protein, or any integer between those values. For example, a protein may be administered to a subject at a dose of about 0.1 μg to about 200 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, or from about 1 mg to about 2 mg, with optional boosters given at, for example, 1 week, 2 weeks, 3 weeks, 4 weeks, two months, three months, 6 months and/or a year later.

In some embodiments, an effective amount of an antibody composition for passive immunization ranges from about 0.001 to about 30 mg/kg body weight, for example, about 0.01 to about 25 mg/kg body weight, about 0.1 to about 20 mg/kg body weight, about 1 to about 10 mg/kg, or about 10 mg/kg to about 20 mg/kg.

A lipidated fusion protein, composition, vaccine, antigen or antibody may also be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). For prophylactic purposes, the amount of lipidated fusion protein in each dose is selected as an amount which induces an immunoprotective response without significant adverse side effects in a typical vaccine. Following an initial vaccination, subjects may receive one or several booster immunisations adequately spaced.

It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combinations, and severity of the particular condition.

Kits

Kits are provided for preventing or treating SP infection and/or SP-associated diseases, comprising one or more recombinant lipidated PsaA fusion protein, antigen, antibody, composition, and/or vaccine as described herein. Instructions for use or for carrying out the methods described herein may also be provided in a kit. A kit may further include additional reagents, solvents, buffers, adjuvants, etc., required for carrying out the methods described herein.

As used herein, the singular forms "a", "an" and "the" include plural references unless the content clearly dictates otherwise.

As used herein, the term "about" refers to a value that is within the limits of error of experimental measurement or determination. For example, two values which are about 5%, about 10%, about 15%, or about 20% apart from each other, after correcting for standard error, may be considered to be "about the same" or "similar". In some embodiments, "about" refers to a variation of ±20%, ±10%, or ±5% from the specified value, as appropriate to perform the disclosed methods or to describe the disclosed compositions and methods, as will be understood by the person skilled in the art.

The technology described herein is not meant to be limited to particular methods, reagents, compounds, compositions or biological systems, which can, of course, vary. It should also be understood that terminology used herein is for the purpose of describing particular aspects only, and is not intended to be limiting.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the present technology.

Example 1. Expression of Lipidated Fusion Protein, Rlipo-PsaA

A recombinant lipidated fusion protein (rlipo-PsaA) including the native PsaA lipid signal sequence, with the sequence described in FIG. 1A (SEQ ID NOs: 1, 7, 9; rlipo-PsaA) was expressed and characterized. We report hereinbelow that this recombinant lipidated fusion protein was able to induce mucosal immunity and skew the immune response toward Th1, and was able to protect mice against *S. pneumoniae* (SP)-associated disease. A nonlipidated PsaA-Ct (PsaA without the lipid signal peptide; rPsaA-Ct) (FIG. 1*b*) was also produced for comparison with the efficacy of rlipo-PsaA. In addition, truncated pneumococcal surface protein A (PspAΔCBD; FIG. 1*c*) and pneumococcal surface protein C (PspCΔCBD; FIG. 1*d*) were produced and were found to increase vaccine efficacy.

For expression and characterization of rlipo-PsaA, the amino-acid sequence of PsaA was obtained from a publicly-available database, and the accession number of PsaA is NP_359087. In order to increase the production yield, we used the codon usage of *Escherichia coli* (*E. coli*) to optimize the DNA sequence for PsaA expression. The PsaA gene was fully synthesized by a biotechnology company and was cloned into the expression vector pET-22b(+) (Novagen, Madison, Wis., USA) using Nde I and Xho I sites to produce the pPsaA plasmid. As a result, the C-terminus of the recombinant protein contained an additional hexahistidine (His6) tag (FIG. 1A). To obtain the PsaA without signal peptide, we constructed the pPsaA-Ct plasmid by a similar method.

The expression plasmid pPsaA-Ct was transformed into *E. coli* strain BL21(DE3) (Invitrogen, Carlsbad, Calif., USA) for protein expression. The transformed cells were cultured at 37° C. overnight and then induced with 1 mM of IPTG for 3 hours (h). To obtain the plasmid for expressing lipidated immunogen, the pPsaA was transformed into *E. coli* strain C43(DE3) (Invitrogen, Carlsbad, Calif., USA) for lipo-protein expression. The transformed cells were cultured at 37° C. overnight and then induced with 1 mM of IPTG at 12° C. for 3 days.

After the pPsaA was transformed into *E. coli* strain C43(DE3), the transformed cells were amplified in 5 ml of Luria-Bertani (LB) broth at 37° C. overnight. Overnight culture was then transferred into 1000 ml of M9 medium (9 mM NaCl, 22 mM $KH_2PO_4$, 47.8 mM $Na_2HPO_4$, 19 mM $NH_4Cl$, 2 mM $MgSO_4$, 0.1 mM $CaCl_2$ and 0.4% Glucose) and cultured at 37° C. After the bacteria reached late log-phase (OD 600 nm~0.7), protein expression was induced by addition of 1 mM isopropylthio-β-D-galactoside (IPTG) at 20° C. for 20 hours.

Example 2. Production and Characterization of Rlipo-PsaA

Non-lipidated form of the antigen (rPsaA-Ct) expressed from pPsaA-Ct, and rlipo-PsaA expressed from pPsaA, were isolated from BL21(DE3) and C43(DE3) cells, respectively, by immobilized metal affinity chromatography (IMAC), as follows. *E. coli* cells were harvested from 4-liter cell cultures by centrifugation (8000×g for 20 min) and the pellets thus collected were re-suspended in 100 ml of a homogenization buffer containing 50 mM Tris (pH 8.0). The *E. coli* cells were then disrupted using a French Press (Constant Systems, Daventry, UK) at 27 Kpsi in the presence of a detergent and the cell lysates thus obtained were centrifuged at 80,000×g for 60 min. The pellet was collected and solubilized using extraction buffer (1% Triton X-100/50 mM Tris (PH8.9)). After centrifugation at 80000×g for 40 min, the supernatant was incubated with 5 mL Ni-NTA resin (Qiagen, San Diego, Calif., USA) in the cold room overnight. The incubated sample and resin slurry were loaded onto a column (1.6 cm i.d.×2.7 cm). The column was washed first with 50 mL of extraction buffer. Recombinant proteins were eluted with the elution buffer (1% Triton X-100; 50 mM Tris (PH8.9)) and characterized by both SDS-PAGE and immunoblotting. The results thus obtained (which are shown in FIG. 2A) indicate that recombinant lipo-E7m was isolated with high purity. The removal of lipopolysaccharide (LPS) was achieved using IMAC coupled with copper ions and extensively washed with 1000 mL of elution buffer and 300 mL of washing buffer (100 mM imidazole; 1% Triton X-100; 50 mM Tris (pH 8.9)). The residue of LPS in the preparation was less than 30 EU/mg.

Figure 2B:
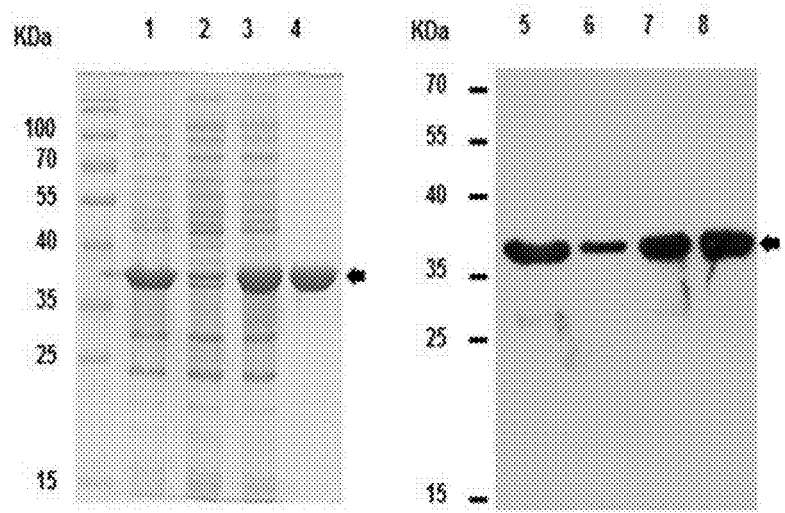
Figure 2C:
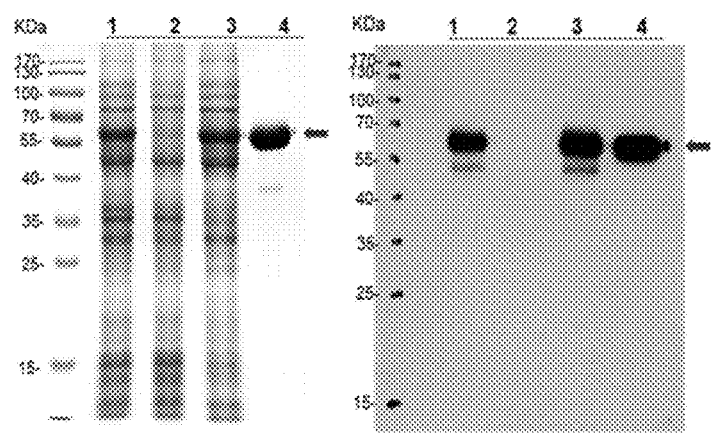
Figure 2D:
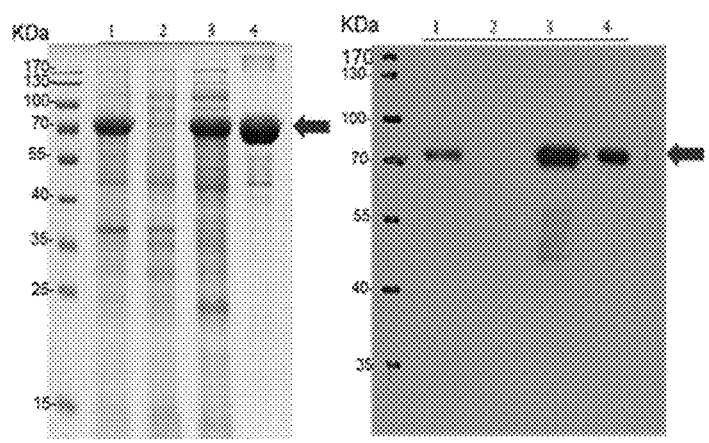

A similar method was used to obtain rPsaA-Ct (FIG. 2B), rPspAΔCBD (FIG. 2B) and rPspCΔCBD (FIG. 2B).

Figure 3A:
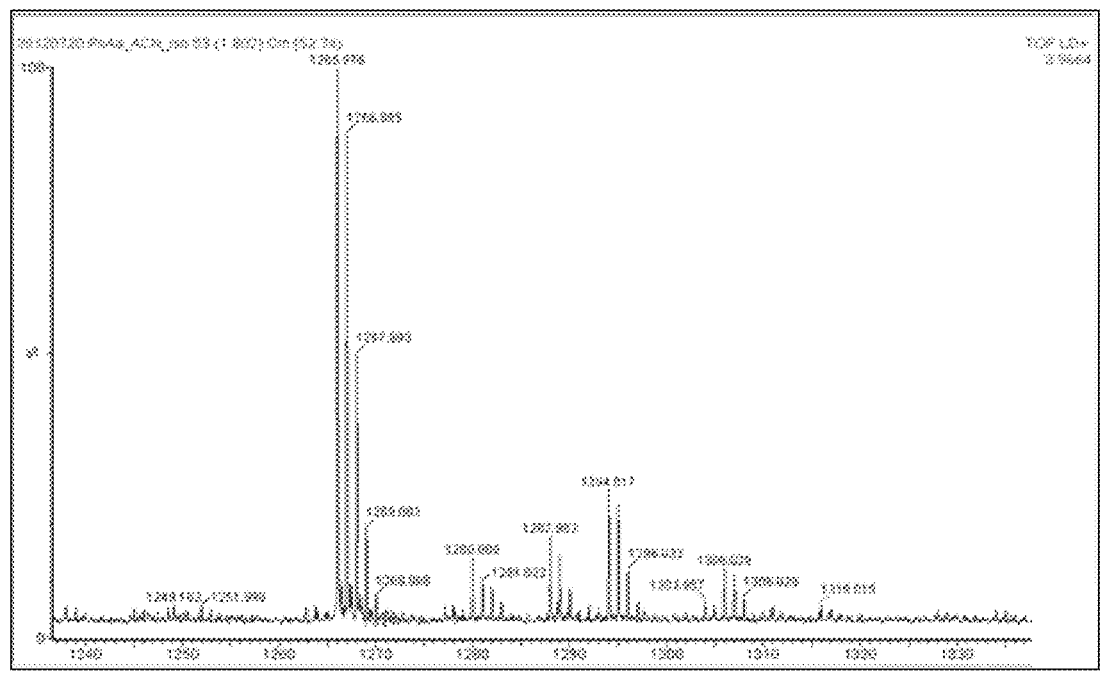
FIGS. 3A-3D show the identification of the N-terminal fragments of rlipo-PsaA and the activation of bone-marrow derived dendritic cells (BMDC) by rlipo-PsaA.

Rlipo-PsaA was subjected to mass spectrometry (MS) analysis as described below. To identify the N-terminal fragment of rlipo-PsaA, rlipo-PsaA was first dialyzed against 5 mM ammonium bicarbonate at pH 8.5 and then treated with trypsin (Promega Co., Madison, Wis., USA) at a rlipo-PsaA:trypsin ratio of 50:1 (wt/wt) in 25 mM ammonium bicarbonate (pH 8.5) for 5 min at room temperature. The enzymatic reaction was terminated by addition of formic acid (final concentration 1.2%). The reaction mixture was further prepared using Ziptip™ (EMD Millipore, Darmstadt, Germany). One µl of the typsin-digested protein was mixed with 1 µl of a saturated solution of α-ciano-4-hydrozycinnamic acid (Sigma, St. Louis, Mich., USA) in acetonitrile/0.1% trifluoroacetic acid (1:3, vol/vol). One microliter of the mixture was placed on the target plate of a matrix-assisted laser desorption ionization time-of-flight (MALDI-TOF) mass spectrometer (Bruker, Madison, Wis., USA) for analysis. Results obtained from MALDI-TOF analysis as described above indicated that the partial trypsin digestion products correspond to the N-terminal fragments of rlipo-PsaA and that these peptides are lipidated (FIG. 3A).

Example 3. Immunogenicity Study of Rlipo-PsaA

Figure 3B:
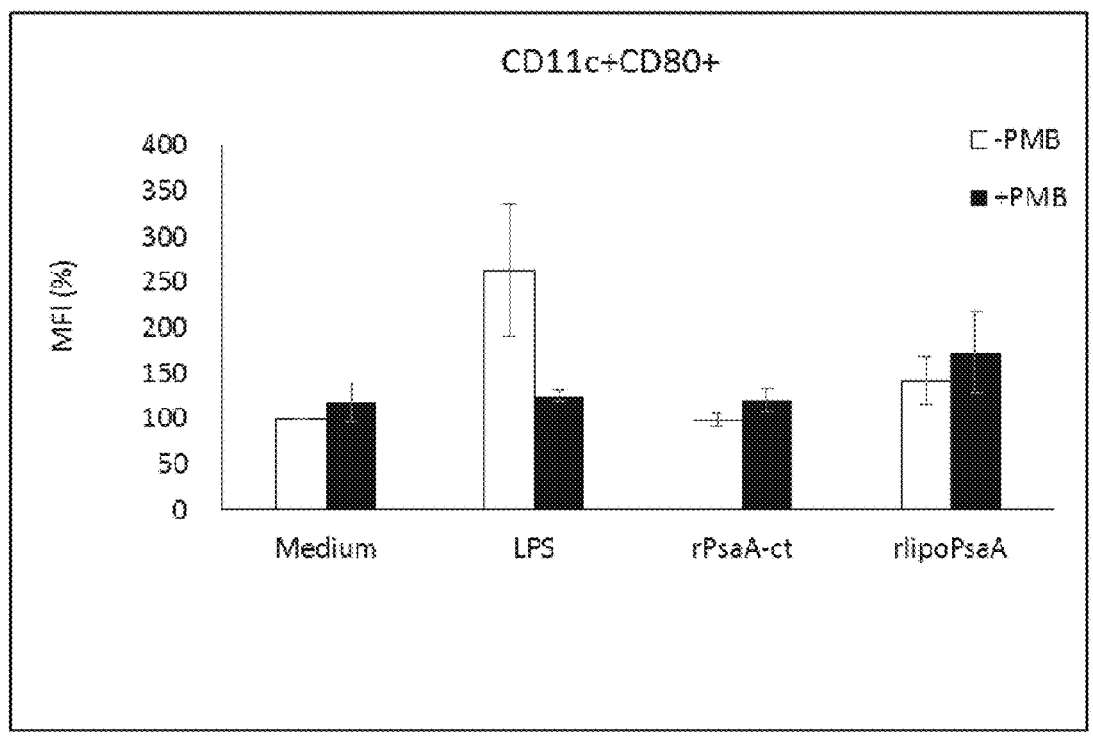
Figure 3C:
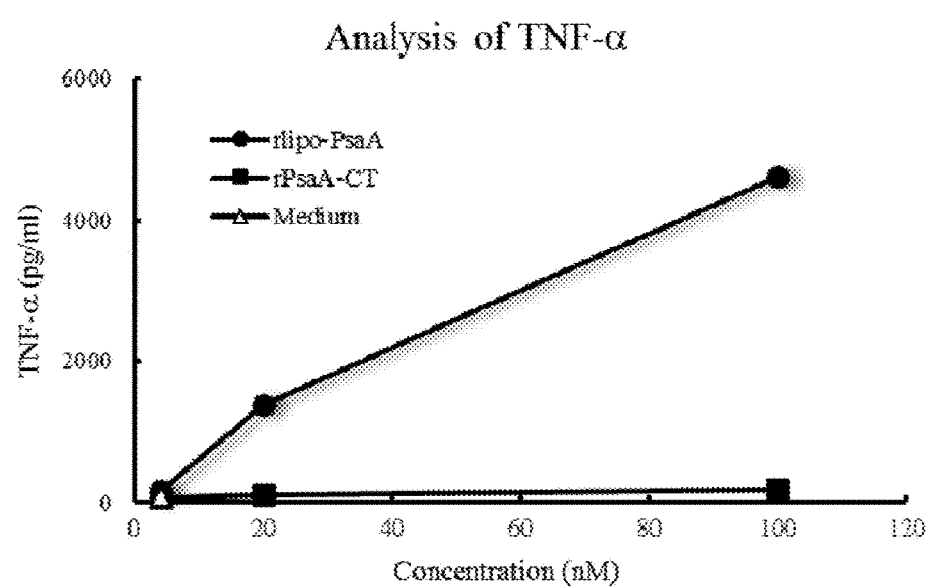
Figure 3D:
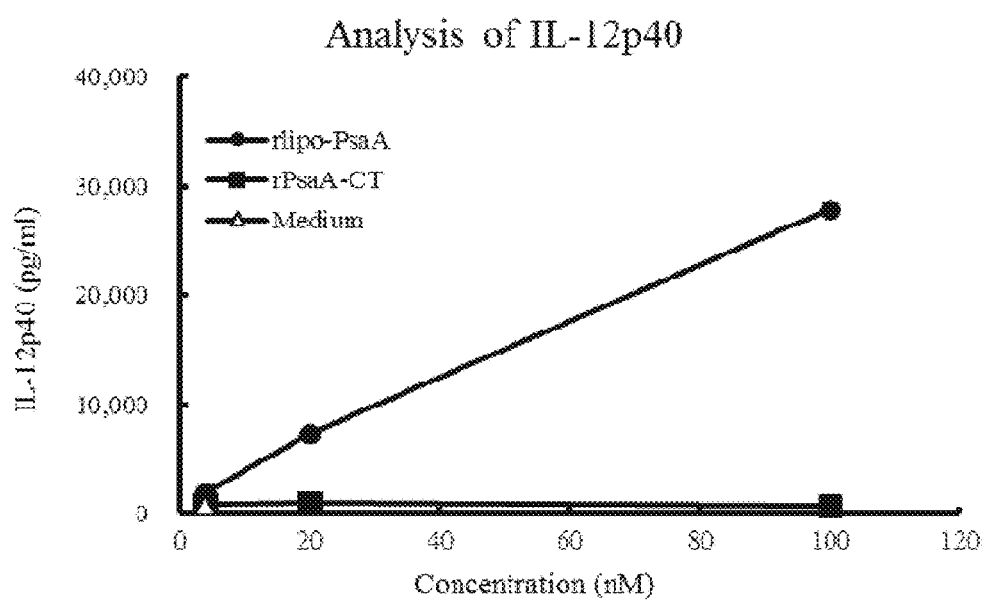

BM-DCs was used as a model to study the immuno-stimulatory properties of rlipo-PsaA. Rlipo-PsaA up-regulated the expression of the surface marker CD80, whereas rPsaA-Ct had no effect (FIG. 3B). Similar results were obtained in cytokine secretion studies. The secretion of TNF-α (FIG. 3C) and IL-12p40 (FIG. 3D) was induced by rlipo-PsaA but not by rPsaA-Ct group (FIGS. 3C and 3C). These results indicate that the immuno-stimulatory activity of rlipo-PsaA was linked to its lipid moiety.

Figure 4A:
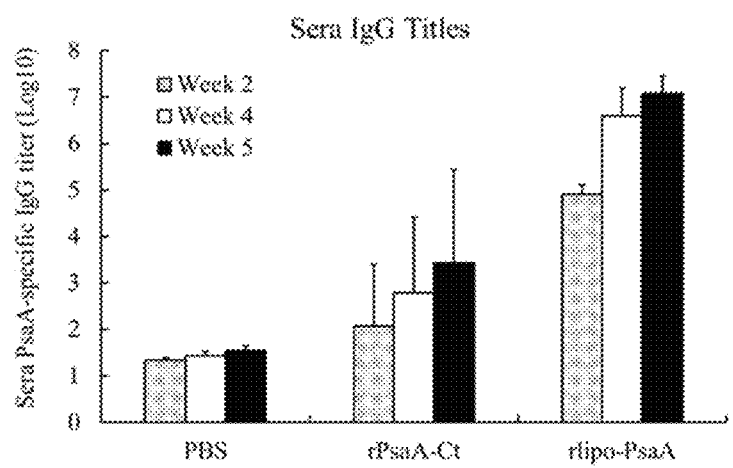
FIGS. 4A-4D show enhancement of anti-PsaA IgG and IgA antibody titers, and induction of a Th1-biased immune response after administration of rlipo-PsaA.
Figure 4B:
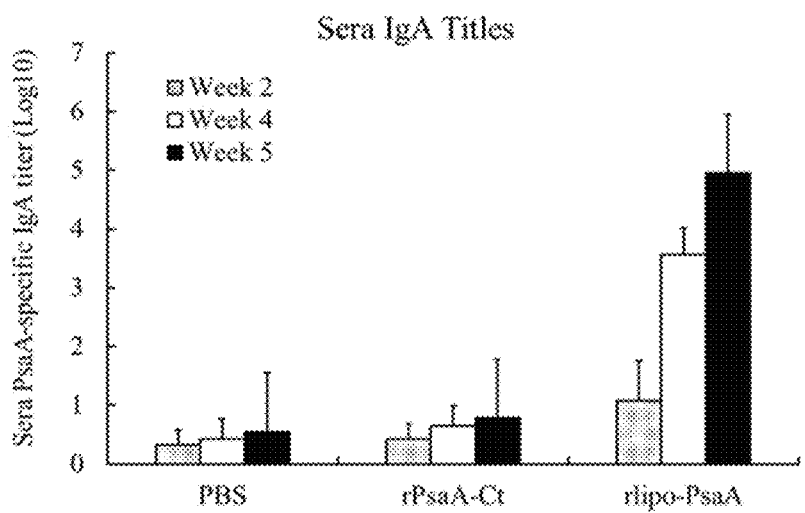
Figure 4C:
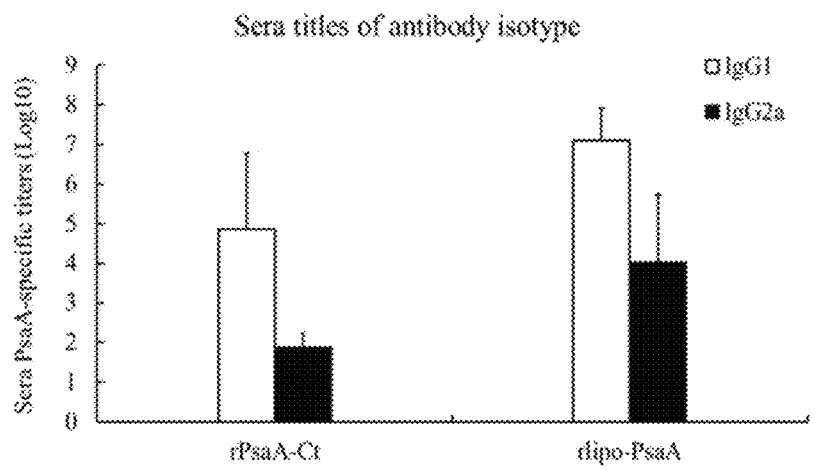
Figure 4D:
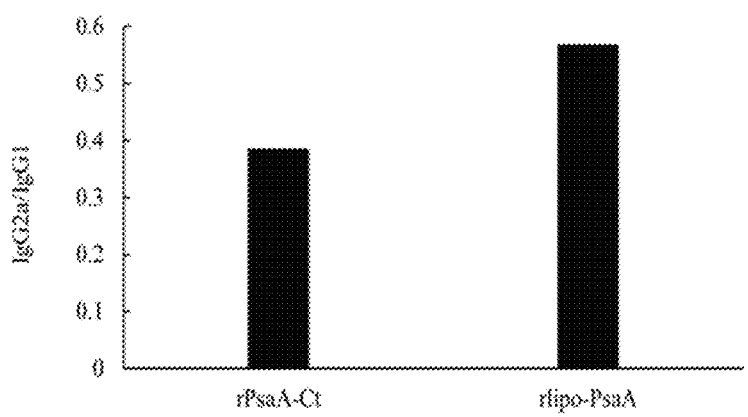

Example 4. Immunization with Rlipo-PsaA Enhances Antigen-Specific IgG and IgA, and Generates a Th1-Biased Response To evaluate the intrinsic adjuvant properties of rlipo-PsaA in vivo, we analyzed the magnitude of the antigen-specific antibody response in mice immunized with either rlipo-PsaA or rPsaA-Ct (FIG. 4A). Mice were immunized twice by subcutaneous injection of 30 µg of rlipo-PsaA in PBS or of 30 µg of rPsaA-Ct in PBS at two-week intervals. The IgG titers elicited by rlipo-PsaA were 1000-fold higher than those elicited by rPsaA-Ct at week 2, 4 and 5 (FIG. 4A). The IgA titers elicited upon immunization with rlipo-PsaA were 10000-fold higher than those elicited by rPsaA-Ct at week 2, 4 and 5 (FIG. 4B). Subsequently, to analyze the antibody isotypes elicited upon immunization with rlipo-PsaA and rPsaA-Ct at week 5, the induced levels of IgG1 and IgG2b were measured. The IgG1 levels were comparable in both rlipo-PsaA- and rPsaA-Ct-immunized mice. The IgG2b levels in the rlipo-PsaA-immunized mice were higher than those in the rPsaA-Ct-immunized mice (FIG. 4C). The Th1-biased phenomenon can be clearly observed by comparing the IgG2b/IgG1 ratios in these mice (FIG. 4D).

Example 5. In Vivo Protection Experiments

We report herein studies using a mouse model, in which mice were vaccinated with immunogens and then challenged with different strains of S. pneumoniae (SP).

Figure 5A:
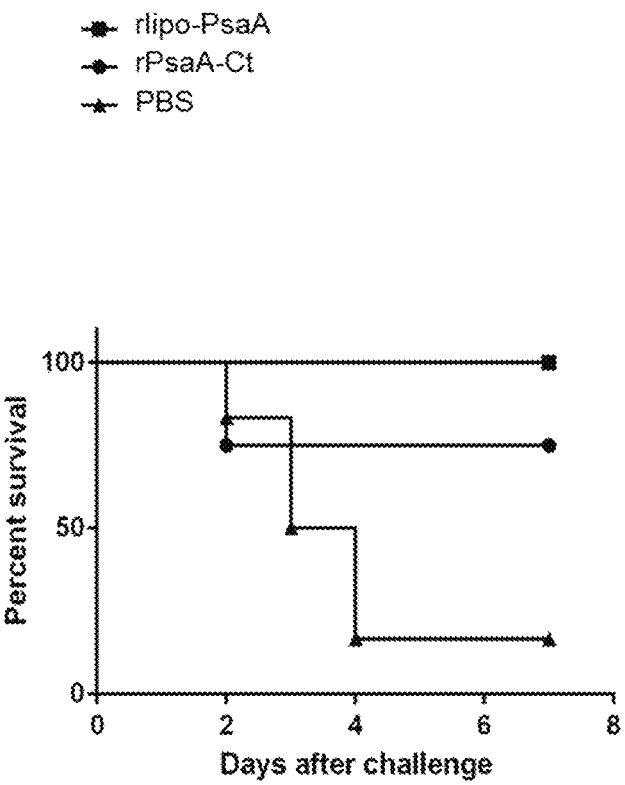
FIGS. 5A-5F show that immunization with rlipo-PsaA and other vaccine candidates protected mice against SP in an animal model.
Figure 5B:
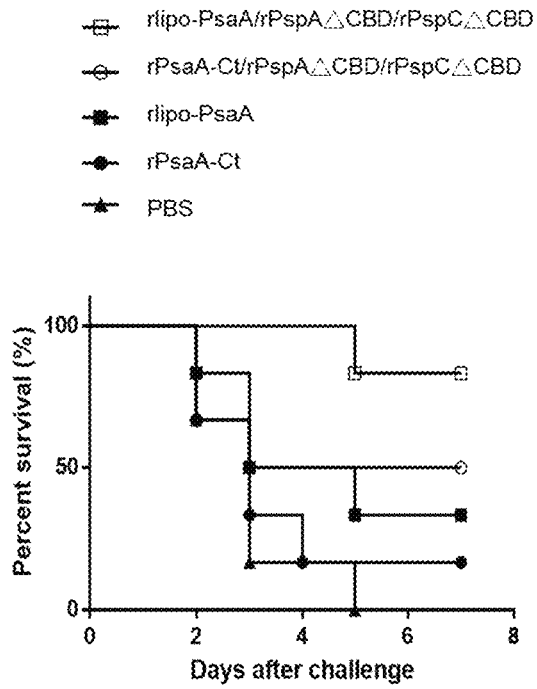
Figure 5C:
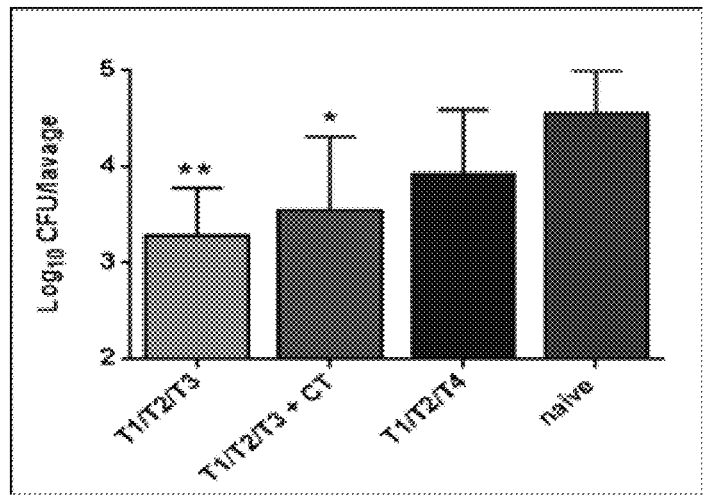
Figure 5D:
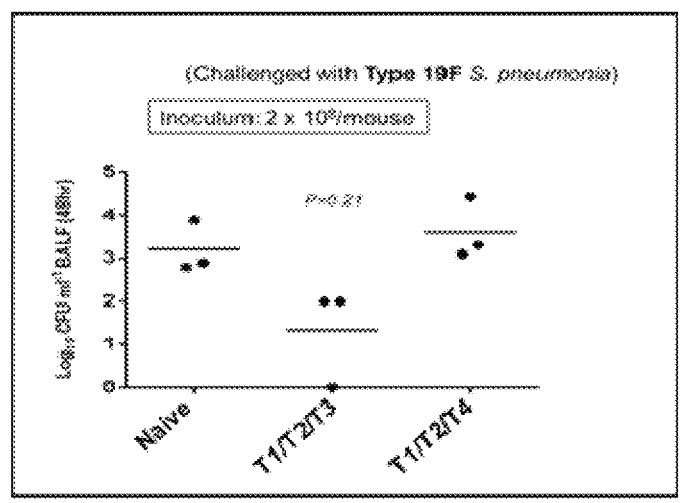
Figure 5E:
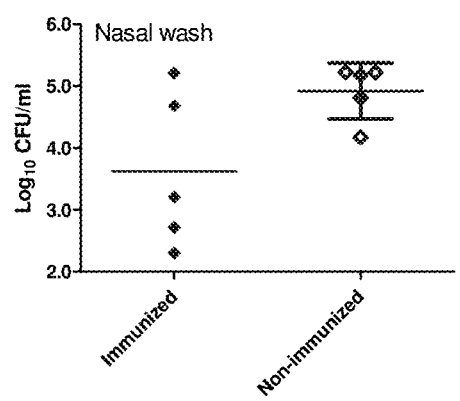
Figure 5F:
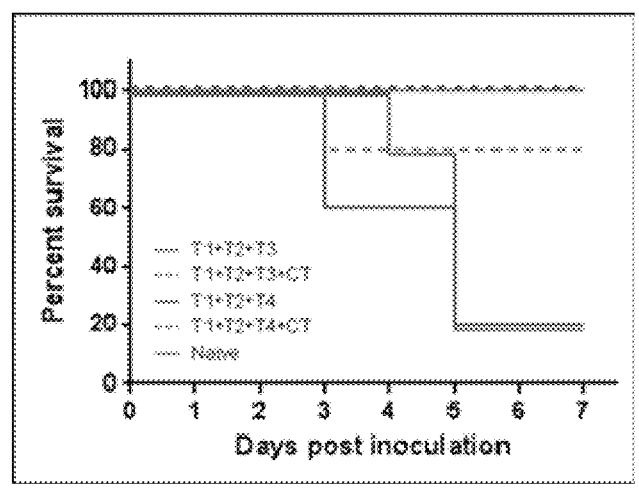

For in vivo protection experiments, ICR mice (six mice per group) were immunized with 30 µg of rlipo-PsaA or rPsaA-Ct. In the first study, the mice were vaccinated with rlipo-PsaA and rPsaA-Ct, and then, were challenged using 10×LD dose of SP. The mice challenged with 2×105 D39 strain (high virulence strain) showed 100% protection after having been immunized with rlipo-PsaA and about 75% protection was seen for those immunized with rPsaA (FIG. 5A). In the second study, the mice were vaccinated with rlipo-PsaA/rPspAΔCBD/rPspCACBD, rPsaA-Ct/rPspAΔCBD/rPspCΔCBD, rlipo-PsaA, rPsaA-Ct and PBS, and then, were challenged using 100×LD dose of SP. The mice challenged with 3.9×106 D39 strain showed 83.3%, 50%, 33.3%, 16.7% and 0% protection, respectively (FIG. 5B).

These results demonstrate that mice immunized with 30 µg of rlipo-PsaA were 100% protected against a challenge with $2\times10^5$ cfu/mL of D39 strain (high virulence strain). The protection rate was found to be about 75% for those mice immunized with rPsaA alone (FIG. 5a). These data indicated that the rlipo-PsaA could induce a significantly stronger protective immunity than rPsaA, and more importantly that vaccinated animals were protected against the challenge from different strains of SP.

We tested whether rlipo-PsaA could confer protection against a higher challenge dose ($100\times LD_{50}$, $3.9\times10^6$ cfu/mL of D39 strain), rlipo-PsaA and other antigens including truncated rPspAΔCBD and rPspCΔCBD. These were assessed in the animal challenge studies for which the results were impressive, with >80% protection found in the group vaccinated with rlipo-PsaA/rPspAΔCBD/rPspCΔCBD, whereas the protection rates in the groups immunized either with rPsaA-Ct/rPspAΔCBD/rPspCΔCBD, or rlipo-PsaA, rPsaA-Ct or PBS were found to be 50%, 33%, 16% and 0%, respectively (FIG. 5b). These results indicate than recombinant lipidated fusion proteins described herein can be used for development of a protein-based pneumococcal vaccine.

To determine the potential protection of the recombinant lipidated fusion proteins against different serotypes of S. pneumoniae, the vaccinated mice were also challenged with an additional 4 different serotypes (type 3, 14, 19F, and 35B) of the bacterial strains. As shown in FIG. 5, in addition to the protection against serotype 2 (FIGS. 5a and 5b), the vaccine either significantly reduced the nasopharyngeal colonization by S. pneumoniae serotypes 14, 19F and 35B, or prevented a lethal invasive infection by serotype 3 (FIGS. 5C-5F). These data indicate that the recombinant lipidated fusion proteins described herein can provide broad protection against infections caused by multiple serotypes of S. pneumoniae.

Example 6. Characterization of Lipid Structure of Rlipo-PsaA

Figure 6A:
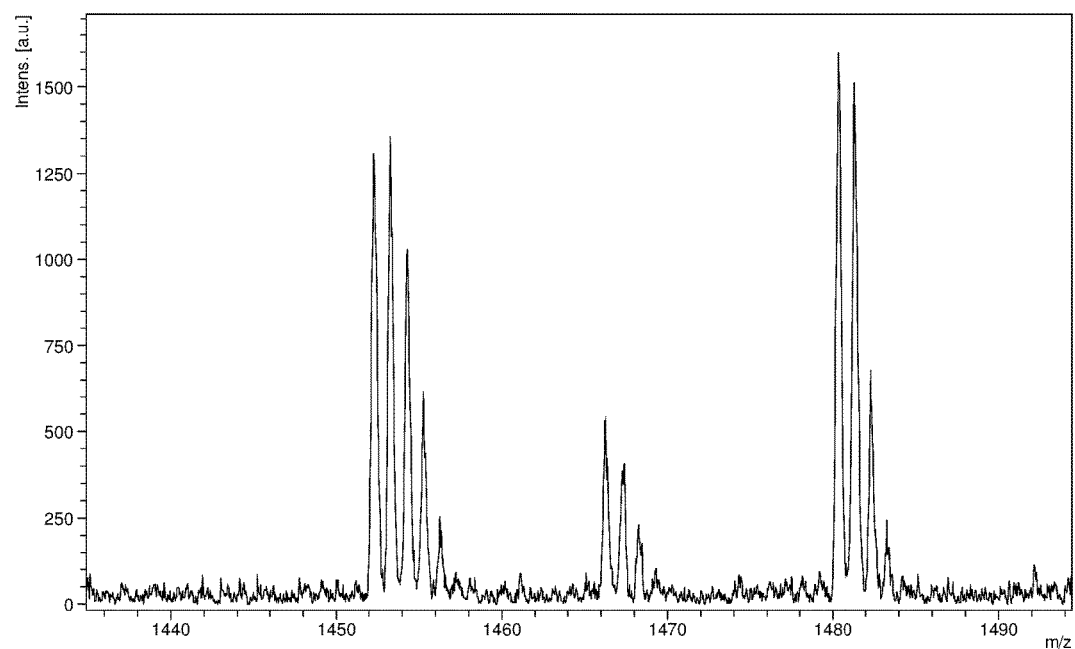
FIGS. 6A-6E show an analysis using mass spectrometry of the lipid structures found on recombinant lipidated fusion proteins.
Figure 6B:
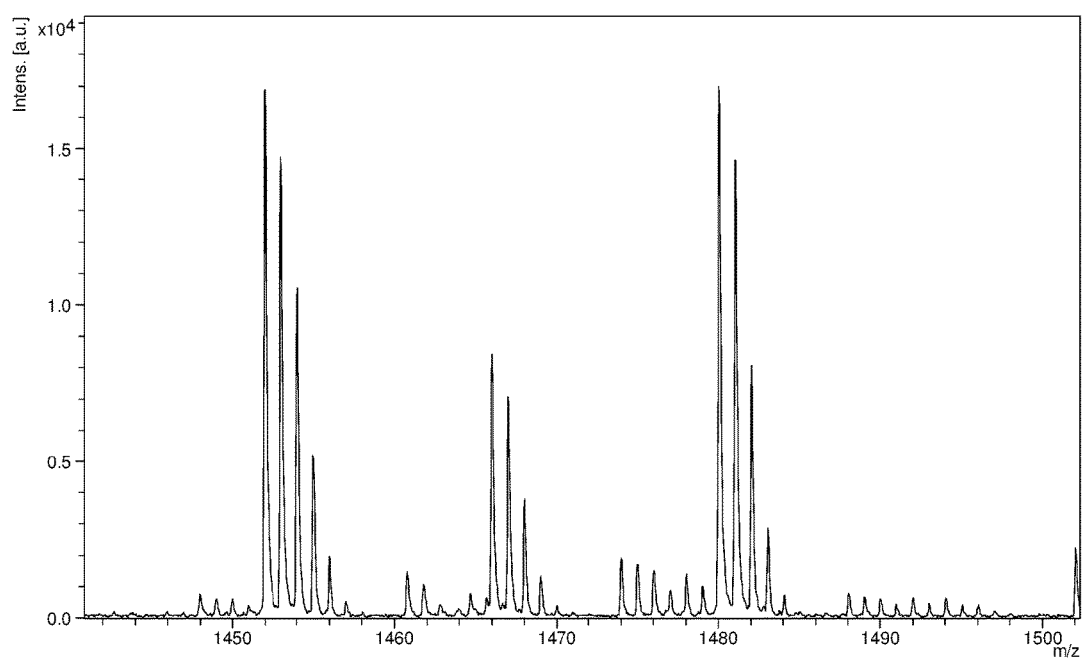
Figure 6C:
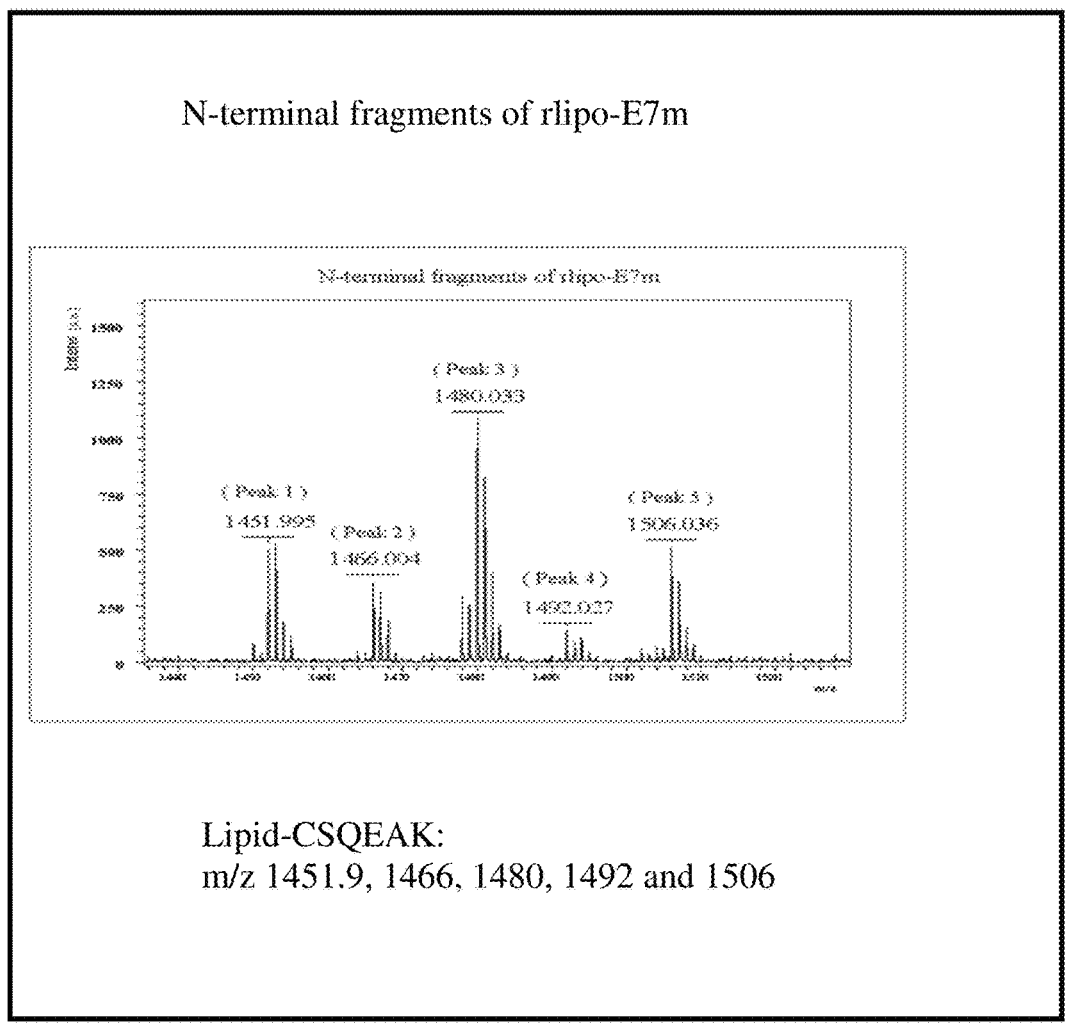
Figure 6D:
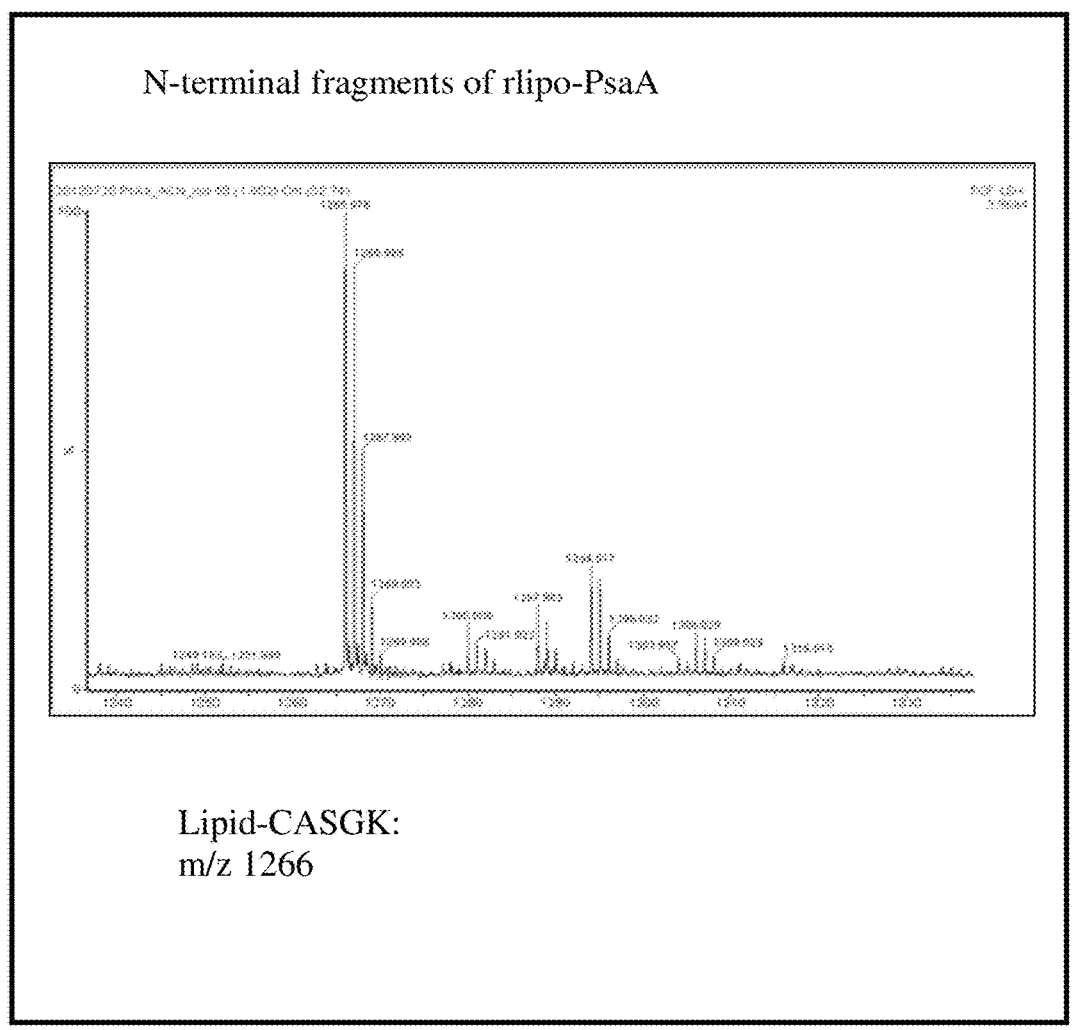
Figure 6E:
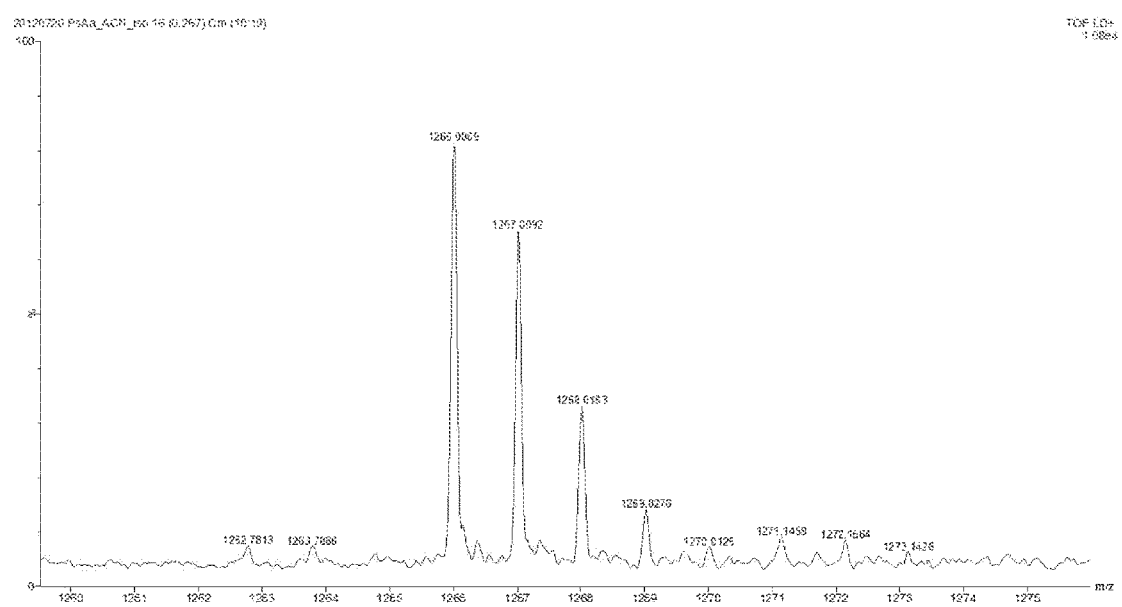

Mass spectrometry was used to characterize the lipid structure of rlipo-PsaA and to compare to lipid structures of other lipidated SP antigens produced in E. coli using heterologous lipid signal peptides. The lipid signal peptide from meningococcal protein Ag473 (having lipid signal peptide sequence: MKKLLIAAMMAAALAAC) expressed in an E. coli system resulted in at least three peaks as analyzed by mass spectrometry (FIG. 6A). The antigens D1E3 and E7m fused with the lipid signal peptide of Ag473 also contained at least three peaks (FIGS. 6B, 6C). In contrast, rlipo-PsaA, expressed using its own native lipid signal peptide (SEQ ID NO: 6), expressed as one major peak (molecular weight) in an E. coli system (FIGS. 6D, 6E, which show results from different batches of rlipo-PsaA). For more information on the molecular structure of lipid moieties, see Proteomics, 2011 11(13):2620-7. These results indicate that, surprisingly, only a single form of lipid modification was expressed on the rlipo-PsaA.

To further characterize the lipid moiety of rlipo-PsaA, the tryptic fragments were measured using MALDI-TOF mass spectrometry. rlipo-PsaA was digested with trypsin for three days at 37° C., and the N-terminal fragments in the reaction mixture were further purified using Ziptip (Millipore, Mass., USA) after trypsin digestion. The mixture or purified tryptic fragments were mixed with a saturated solution of α-ciano-4-hydroxycinnamic acid in acetonitrile/0.1% trifluoroacetic acid (1:3, vol/vol). The mixture was placed on the target plate of a MALDI-TOF instrument (Waters, Milford, Mass., USA) for analysis. As mentioned above, FIGS. 6D and 6E show the results from two different batches of rlipo-PsaA.

We confirmed that the peaks of rlipo-PsaA were associated with the lipidated cysteine residue and verified that rPsaA contained a bacterial lipid moiety at its N-terminus. The exact mass of N-terminal fragments of rlipo-PsaA was 1266, which is the cystinyl-lipid-moiety with Ala-Ser-Gly-Lys. Based on the exact mass of the N-terminal fragment, it was determined that the signal sequence was processed and the lipid structure was triacyl-lipopeptide (C16:0, C17:1, C16:0), specifically the lipid modification was N-acyl-S-diacylglycerol (linked to cysteine). The N-terminal fragment of rlipo-PsaA was thus N-acyl-S-diacylglycerol cysteine-Ala-Ser-Gly-Lys.

It is noted that this unique triacyl-Cys-Ala-Ser-Gly-Lys peptide sequence is distinct from other known recombinant lipidated fusion proteins which have unsaturated lipid moieties (C16 to C19) at the R2 position after the signal sequence is processed and cleaved.

In summary, using the methods described herein we have expressed recombinant lapidated PsaA using its own signal sequence and obtained much higher yield than obtained previously. We determined the exact mass of the N-terminal fragment of rlipo-PsaA and demonstrated that the lipid modification is N-acyl-S-diacylglycerol cysteine. In addition, the lipid modification of rlipo-PsaA produced using the methods described herein is significantly more homogeneous than other recombinant fusion lipidated proteins and may provide significant improvements for industrial production of recombinant lipidated PsaA.

Although this invention is described in detail with reference to preferred embodiments thereof, these embodiments are offered to illustrate but not to limit the invention. It is possible to make other embodiments that employ the principles of the invention and that fall within its spirit and scope as defined by the claims appended hereto.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

The contents of all documents and references cited herein are hereby incorporated by reference in their entirety.

What is claimed is:

1. A recombinant lipidated fusion protein comprising pneumococcal surface antigen A (PsaA), wherein the recombinant lipidated fusion protein comprises the C-terminal structural gene for PsaA after cleavage of the N-terminal signal peptide, wherein the C-terminal structural gene is lipid-modified with triacyl (C16:0, C17:1, C16:0).

2. The recombinant lipidated fusion protein of claim 1, wherein the lipid modification is N-acyl-S-diacylglycerol linked to cysteine at the N-terminus of the recombinant lipidated fusion protein.

3. The recombinant lipidated fusion protein of claim 1, wherein the N-terminal sequence of the recombinant lipidated fusion protein is N-acyl-S-diacylglycerol cysteine-Ala-Ser-Gly-Lys (SEQ ID NO: 10).

4. The recombinant lipidated fusion protein of claim 1, wherein the recombinant lipidated fusion protein further comprises a tag or a detectable label at the C-terminus.

5. The recombinant lipidated fusion protein of claim 4 wherein the tag is an amino acid tag comprising 6 Histidine residues (SEQ ID NO: 11).

6. The recombinant lipidated fusion protein of claim 1, wherein the recombinant lipidated fusion protein comprises the amino acid sequence set forth in SEQ ID NO: 9.

7. The recombinant lipidated fusion protein of claim 1, wherein the recombinant lipidated fusion protein comprises an amino acid sequence at least about 80-95% identical to the amino acid sequence set forth in SEQ ID NO:9.

8. The recombinant lipidated fusion protein of claim 1, wherein the recombinant lipidated fusion protein is produced in *E. coli*.

9. The recombinant lipidated fusion protein of claim 8, wherein the recombinant lipidated fusion protein is produced by expression of a vector comprising the DNA having the nucleotide sequence set forth in SEQ ID NO: 6.

10. The recombinant lipidated fusion protein of claim 1, wherein the recombinant lipidated fusion protein comprises a homogeneous lipid structure.

11. The recombinant lipidated fusion protein of claim 10, wherein the homogeneous lipid structure comprises a single major peak as analyzed by mass spectrometry or has the mass spectrometry spectrum shown in FIG. 6D or FIG. 6E.

12. The recombinant lipidated fusion protein of claim 11, wherein the single major peak has a m/z of about 1266.

13. The recombinant lipidated fusion protein of claim 1, wherein the recombinant lipidated fusion protein is capable of inducing a mucosal immune response against an *Streptococcus pneumoniae*-associated disease in a subject.

14. The recombinant lipidated fusion protein of claim 13, wherein a Th1 response and/or production of secretory IgA is induced in the subject.

15. The recombinant lipidated fusion protein of claim 14, wherein the recombinant lipidated fusion protein is capable of inducing the mucosal immune response when administered in the absence of an adjuvant.

16. The recombinant lipidated fusion protein of claim 13, wherein the recombinant lipidated fusion protein is further capable of causing a mucosal immune response to be induced against one or more non-lipidated *Streptococcus pneumoniae* (SP) antigen administered concomitantly.

17. The recombinant lipidated fusion protein of claim 16, wherein the one or more non-lipidated SP antigen is selected from pneumococcal surface protein A (PspA), pneumococcal surface protein C (PspC), pneumococcal beta-galactosidase (BgaA), pneumococcal phosphorylcholine (ChoP), pneumococcal enolase (Eno), pneumococcal hyaluronate lyase (Hyl), pneumococcal autolysin A (LytA), pneumococcal neuraminidase (Nan), pneumococcal adhesion and virulence A (PavA), pneumococcal iron acquisition (PiaA), and pneumococcal surface association of Pht Proteins (PhtA, PhtB, PhtD, and PhtE).

18. The recombinant lipidated fusion protein of claim 13, wherein the mucosal immune response is not serotype-specific.

19. The recombinant lipidated fusion protein of claim 13, wherein the *Streptococcus pneumoniae*-associated disease is pneumonia, *meningitides*, ear infection, sinus infection, or bacteremia.

20. A method of producing the recombinant lipidated fusion protein according to claim 1, the method comprising the steps of:
  (1) providing a host *E. coli* cell transformed with an expression vector that comprises a first nucleotide sequence encoding the N-terminal native lipid signal peptide of PsaA and a second nucleotide sequence encoding the C-terminal structural gene for PsaA; and
  (2) cultivating the *E. coli* transformant to allow expression of the fusion protein comprising the N-terminal native lipid signal peptide of PsaA and the C-terminal structural gene for PsaA.

21. The method of claim 20, wherein the host *E. coli* cell is from a strain that provides high-level protein expression selected from C43(DE3), (ECCC B96070445), C41(DE3) (ECCC B96070444), C0214(DE3), DK8(DE3)S (NCIMB 40885), and C2014(DE3) (NCIMB 40884).

22. A composition comprising the recombinant lipidated fusion protein according to claim 1 and a pharmaceutically acceptable diluent, carrier, or excipient.

23. The composition of claim 22, wherein the composition further comprises one or more non-lipidated SP antigen selected from pneumococcal surface protein A (PspA), pneumococcal surface protein C (PspC), pneumococcal beta-galactosidase (BgaA), pneumococcal phosphorylcholine (ChoP), pneumococcal enolase (Eno), pneumococcal hyaluronate lyase (Hyl), pneumococcal autolysin A (LytA), pneumococcal neuraminidase (Nan), pneumococcal adhesion and virulence A (PavA), pneumococcal iron acquisition (PiaA), and pneumococcal surface association of Pht Proteins (PhtA, PhtB, PhtD, and PhtE).

24. A method for preventing or treating an SP-associated disease comprising administering to a subject the recombinant lipidated fusion protein according to claim 1, such that the SP-associated disease is prevented or treated in the subject.

25. A composition comprising the recombinant lipidated fusion protein according to claim 1 and an adjuvant.

* * * * *